US007507872B2

(12) United States Patent
Akira et al.

(10) Patent No.: US 7,507,872 B2
(45) Date of Patent: Mar. 24, 2009

(54) TRANSGENIC TOLL-LIKE RECEPTOR 9 (TLR9) MICE

(75) Inventors: Shizuo Akira, Takatsuki (JP); Hiroaki Hemmi, Ibaraki (JP)

(73) Assignee: Japan Science and Technology Agency, Saitama (JP)

( * ) Notice: Subject to any disclaimer, the term of this patent is extended or adjusted under 35 U.S.C. 154(b) by 1067 days.

(21) Appl. No.: 10/088,567

(22) PCT Filed: Jun. 5, 2001

(86) PCT No.: PCT/JP01/04731

§ 371 (c)(1),
(2), (4) Date: Mar. 19, 2002

(87) PCT Pub. No.: WO02/06482

PCT Pub. Date: Jan. 24, 2002

(65) Prior Publication Data

US 2003/0124655 A1 Jul. 3, 2003

(30) Foreign Application Priority Data

Jul. 19, 2000 (JP) .............................. 2000-219652

(51) Int. Cl.
*A01K 67/27* (2006.01)
*C12N 5/00* (2006.01)
(52) U.S. Cl. ........................................ 800/18; 435/325
(58) Field of Classification Search .................. 800/3, 800/8, 18; 435/325
See application file for complete search history.

(56) References Cited

U.S. PATENT DOCUMENTS 4,946,778 A 8/1990 Ladner et al.
6,943,240 B2 * 9/2005 Bauer et al. ................ 536/23.1

FOREIGN PATENT DOCUMENTS

| WO | WO 01/55386 | 8/2001 |
| WO | WO 01/81578 | 11/2001 |
| WO | WO 01/90151 | 11/2001 |
| WO | WO 02/22809 | 3/2002 |
| WO | WO 02/31111 | 4/2002 |

OTHER PUBLICATIONS

Houdebine et al Journal of Biotechnology, 1994, vol. 34, pp. 269-287.*
Houdebine et al, Transgenic Research , 2000, 9: 305-320.*
Cameron et al, Molecular Biotechnology, 1997, 7: 253-265.*
Kolb et al, Gene, 1999, 227: 21-31.*
Holschneider DP and Shih JC. J. Devl Neuroscience, 2000, 18: 615-618.*
Taurog JD, J Immunol. 1988 ;141(11):4020-3.*
Mullins LJ, Mullins JJ. J Clin Invest. 1996 ;97(7):1557-60.*
Campbell KHS and Wilmut I. Theriogenology 1997 , 47:63-72.*
Moreadith RW, Radford NB.J Mol Med. 1997;75(3):208-16.*
Mullins JJ et al EMBO J. 1989;8(13):4065-72.*
Mullins JJ, Peters J, Ganten D. Nature. 1990;344(6266):541-4.*
Hammer RE, Cell. 1990;63(5):1099-112.*
Takeuchi et al Immunity, 1999, 11, 443-452.*
Hemmi et al Nature. Dec. 7, 2000; 408(6813): 740-5.*
Kappel et al Current Opinions in Biotechnology ,1992, 548-553.*
Sigmund CD. Arterioscler Thromb Vasc Biol. 2000;20(6):1425-9.*
Neimann, H. Transgenic Res, 1998, 7: 73-75.*
Wall RJ, Thenogenology, 1996, 45: 57-68.*
Mullins et al Hypertension , 1993, 630-633.*
Wolfer et al Trends in Neuroscience, 2002, 25 (7):336-340.*
Babiuk et al Immunology 2004 113 114-120.*
Griffiths Microscopy Research and Technique 1998, 41: 344-358.*
Keri et al., (Proc Natl Acad Sci U S A. 2000; 97(1): 383-7.*
Schoonjans et al Stem Cells, 2003; 21:90-97.*
Carl Hashimoto et al., "The Toll Gene of Drosophila, Required for Dorsal-Ventral Embryonic Polarity, Appears to Encode a Transmembrane Protein", Cell, vol. 52, 269-279, Jan. 29, 1988.
Marcia P. Belvin et al., "A Conserved Signaling Pathway: The Drosophila Toll-Dorsal Pathway", Annu. Rev., Cell Dev. Biol. 12, pp. 393-416, 1996.
Bruno Lemaitre et al., "The Dorsoventral Regulatory Gene Cassette spätzle/Toll/cactus Controls the Potent Antifungal Response in Drosophila Adults", Cell, vol. 86, pp. 973-983, Sep. 20, 1996.
Scientific Correspondence, Nature 351, pp. 355-356, May 31, 1991.
Luke A. J. O'Neill et al., "Signal transduction pathways activated by the IL-1 receptor family: ancient signaling machinery in mammals, insects, and plants", J. Leukoc. Biol. 63, pp. 650-657, Jun. 1988.
Rusian Medzhitov et al., "A human homologue of the Drosophila Toll protein signals activation of adaptive immunity", Nature, vol. 388, pp. 394-397, Jul. 24, 1997.
Fernando L. Rock et al., "A family of human receptors structurally related to Drosophila Toll", Proc. Acad. Sci. USA 95, pp. 588-593, Jan. 1998.
Preet M. Chaudhary et al., "Cloning and Characterization of Two Toll/Interleukin-1 Receptor-Like Genes TIL3 and TIL4: Evidence for a Multi-Gene Receptor Family in Humans", Blood, vol. 91, pp. 4020-4027, Jun. 1998.

(Continued)

*Primary Examiner*—Thaian N. Ton
*Assistant Examiner*—Anoop K Singh
(74) *Attorney, Agent, or Firm*—King & Spalding, LLP; Kenneth H. Sonnenfeld; Michael A. Willis

(57) ABSTRACT

The present invention provides a receptor protein specifically recognizing bacterial DNA having an unmethylated CpG sequence, a genomic DNA encoding it, an experimental animal model useful for examining responsiveness of a host immune cell against a bacterial infectious disease. DNA encoding a receptor protein specifically recognizing bacterial DNA having an unmethylated CpG sequence is screened by BLAST search, a number of EST clones having high homology with various TLRs is screened, these clones are used as a probe to isolate a full-length cDNA from mouse macrophage cDNA library, and the sequence of bases of the cDNA is analyzed to confirm that it is TLR9 comprising a conserved regions such as LRR and TIR regions, and then a knockout mouse is produced to confirm that TLR9 is a receptor protein of oligonucleotides having an unmethylated CpG sequence of bacterial DNA.

2 Claims, 6 Drawing Sheets

OTHER PUBLICATIONS

O. Takeuchi et al., "TLR6: A novel member of an expanding Toll-like receptor family", Gene 231, pp. 59-65, 1999.

Marta Muzio et al., The Human Toll Signaling Pathway: Divergence of Nuclear Factor KB and JNK/SAPK Activation Upstream of Tumor Necrosis Factor Receptor-associated Factor 6 (TRAF6), J. Exp. Med. 187, pp. 2097-2101, Jun. 15, 1998.

Rusian Medzhitov et al., MyD88 Is an Adaptor Protein in the hToll/IL-1 Receptor Family Signaling Pathways, Molecular Cell, vol. 2, pp. 253-258, Aug. 1998.

Taro Kawai et al., "Unresponsiveness of MyD88-Deficient Mice to Endotoxin", Immunology, vol. 11, pp. 115-122, Jul. 1999.

Rusian Medzhitov et al., "Innate Immunity: The Virtues of a Nonclonal System of Recognition", Cell, vol. 91, pp. 295-298, Oct. 31, 1997.

David C. Morrison et al., "Bacterial Endotoxins and Host Immune Responses", Advances In Immunology, vol. 28, pp. 293-450, 1979.

R.J. Ulevitch et al., "Receptor-Dependent Mechanisms of Cell Stimulation by Bacterial Endotoxin", Annu. Rev. Immunol. vol. 13, pp. 437-457, 1995.

Samuel D. Wright, "CD14, a Receptor for Complexes of Lipopolysaccharide (LPS) and LPS Binding Protein", Science 249, pp. 1431-1433, Sep. 21, 1990.

Katsuaki Hoshino et al., "Cutting Edge: Toll-Like Receptor 4 (TLR4)-Deficient Mice Are Hyporesponisve to Lipopolysaccharide: Evidence for TLR4 as the Lps Gene Product", J. Immunol. 162, pp. 3749-3752, 1999.

Osamu Takeuchi et al., "Differential Roles of TLR2 and TLR4 in Recognition of Gram-Negative and Gram-Positive Bacterial Cell Wall Components", Immunity, vol. 11, pp. 443-451, Oct. 1999.

Arthur M. Krieg, "Lymphocyte activation by CPG dinucleotide motifs in prokaryotic DNA", Trends In Microbiology, vol. 4, No. 2, pp. 73-76, Feb. 1996.

Grayson B. Lipford et al., "Bacterial DNA as immune cell activator" Trends In Microbiology, vol. 6, No. 12, pp. 496-500, Dec. 1998.

Hans Häcker et al. "Cell type-specific activation of mitogen-activated protein kinases by CpG-DNA controls interleukin-12 release from antigen-presenting cells", EMBO J., vol. 18, No. 24, pp. 6973-6982, 1999.

Thilo Jakob et al., "Activation of Cutaneous Dendritic Cells by CpG-Containing Oligodeoxynucleotides: A Role for Dendritic Cells in the Augmentation of Th1 Responses by Immunostimulatory DNA,", J. Immunol. 161, pp. 3042-3049, 1998.

G. Hartman et al., "CpG DNA: A potent signal for growth, activation, and maturation of human dendritic cells", Proc. Natl. Acad. Sci. USA 96, pp. 9305-9310, Aug. 1999.

Hermann Wagner, "Bacterial CpG DNA Activates Immune Cells to Signal Infectious Danger", Adv. Immunol., vol. 73, pp. 329-368, 1999.

Arthur M. Krieg, "The role of CpG motifs in innate immunity", Curr. Opin. Immunol. 12, pp. 35-43, 2000.

"Continuous cultures of fused cells secreting antibody of predefined specificity", Nature vol. 256, pp. 495-497 Aug. 7, 1975.

Danuta Kozbor et al., "The production of monoclonal antibodies from human lymphocytes", Immunology Today, vol. 4, No. 3, p. 72, 1983.

S.P.C. Cole et al., "The EBV-Hybridoma Technique and Its Application to Human Lung Cancer", Monoclonal Antibodies and Cancer Therapy, pp. 77-96, Alan R. Liss, Inc. 1985.

Leonard Davis et al., "Basic Methods In Molecular Biology", 2nd Edition, 1986, cover and bibliographic pages only.

France Pietri-Rouxel et al., "The biochemical effect of the naturally occurring Trp64-Arg mutation on human β3-adrenoceptor activity", Eur. J. Biochem., 247, pp. 1174-1179, 1997.

Shin Takagi et al., "Expression of a Cell Adhesion Molecule, Neuropilin, in the Developing Chick Nervous System", Dev. Biol. 170, pp. 270-222, 1995.

Atsushi Kawakami et al., "Developmentally Regulated Expression of a Cell Surface Protein, Neuropilin, in the Mouse Nervous System", J. Neurobiol., vol. 29, No. 1, pp. 1-17, 1996.

Makoto Matsumoto et al., "A Novel LPS-Inducible C-Type Lectin Is a Transcriptional Target of NF IL6 in Macrophages1", J. Immunol. 163, pp. 5039-5048, 1999.

Kayo Inaba et al., "Generation of Large Numbers of Dendritic Cells from Mouse Bone Marrow Cultures Supplemented with Granulocyte/Macrophage Colony-stimulating Factor", J. Exp. Med., vol. 176, Dec. 1992.

Taro Kawai et al., "Unresponsiveness of MyD88-Deficient Mice to Endotoxin", Immunity, vol. 11, pp. 115-122, Jul. 1999.

Hiroaki Hemmi et al., A Toll-like receptor recognizes bacterial DNA, Nature, vol. 408, pp. 740-745, Dec. 7, 2000.

Xin Du et al., "Three novel mammalian toll-like receptors: gene structure, expression, and evolution" Eur. Cytokine Netw., vol. 11, No. 3, pp. 362-371, Sep. 2000.

Gerard T. Hardiman et al., WO98/50547 (AU 9871754, EP980429).

Elizabeth B. Kopp et al., "The Toll-receptor family and control of innate immunity", Curr. Opin Immunol. 11, pp. 13-18, 1999.

Fernando L. Rock et al., "A family of human receptors structurally related to Drosophila Toll", Proc. Natl. Acad. Sci. USA 95, pp. 588-593, Jan. 1998.

Douglas T. Fearon, "Seeking wisdom in innate immunity", Nature, vol. 388, pp. 323-324, Jul. 24, 1997.

WO99/51259 (AU9934678, EP1067956, US6218371).

Osamu Takeuchi et al., "Cellular responses to bacterial cell wall components are mediated through MYD88-dependent signaling cascades", Int. Immunol. 12, No. 1, pp. 113-117, 2000.

"Molecular Cloning: A Laboratory Manual", 2nd Edition, Cold Spring Harbor Laboratory Press, (cover and bibliographic pages only), 1989.

Hacker et al., Immune Cell Activation by Bacterial CpG-DNA through Myeloid Differentiation Marker 88 and Tumor Necrosis Factor Receptor-Associated Factor (TRAF) 6., J. Exp. Med., Aug. 2000, vol. 192, No. 4, pp. 595-600.

Dennis M. Klinman et al., "Immune Recognition of Foreign DNA: A Cure for Bioterrorism?", Immunity, Aug. 1999, pp. 123-129, vol. 11.

Hans Häcker et al. , "Immune Cell Activation by Bacterial CpG-DNA through Myeloid Differentiation Marker 88 and Tumor Necrosis Factor Receptor-Associated Factor (TRAF)6", J. Exp. Med., Aug. 21, 2000, pp. 595-600, vol. 192, No. 4.

Genbank Accession No. AF 259262 Modification date Feb. 6, 2001: (cited in EP Search Report dated Apr. 28, 2005).

Genbank Accession No. AF 245704 last update: Apr. 15, 2005.

Genbank Accession No. AB 045180—Modification date Feb. 10, 2001.

Genbank Accession No. AF 348140—Modification date Aug. 2, 2001.

Genbank Accession No. AF 314224—Modification date Sep. 24, 2002.

Genbank Accession No. AA 273731 (cited in EP Office Action Nov. 11, 2005).

Zimmerman et al., "Cutting Edge: CpG Oligodeoxynucleotides Trigger Protective and Curative Th1 Responses in Lethal Murine Leishmaniasis," Journal of Immunology, vol. 160, 3627-3630, 1998.

Jakob et al., "Activation of Cutaneous Dendritic Cells by CpG-Containing Oligodeoxynucleotides: A Role for Dendritic Cells in the Augmentation of Th1 Responses by Immunostimulatory DNA," Journal of Immunology, vol. 161, pp. 3042-3049, 1998.

Krieg et al., "CpG DNA Induces Sustained IL-12 Expression In Vivo and Resistance to *Listeria monocytogenes* Challenge," Journal of Immunology, vol. 161, pp. 2428-2434, 1998.

Elkins et al., "Bacterial DNA Containing CpG Motifs Stimulates Lymphocyte-Dependent Protection of Mice Against Lethal Infection with Intracellular Bacteria," Journal of Immunology, vol. 162, pp. 2291-2298, 1999.

Wagner et al., "Immunostimulatory DNA sequences help to eradicate intracellular pathogens," Springer Semin Immunopathol, vol. 22, pp. 147-152, Jun. 2000.

Database EMBL Accession No. AB045181, XP001212803, Dec. 13, 2000.

\* cited by examiner

FIG. 4

```
        87       90            96          100              110
+/+ :  TCC AAC CTG CGG CAG CTG AAC CTC AAG TGG AAC TGT CCA CCC ACT GGC CTT AGC CCC TTG CAC TTC TCT TGC
        S   N   L   R   Q   L   N   L   K   W   N   C   P   P   T   G   L   S   P   L   H   F   S   C
        |   |   |   |   |   |   |   |   |   |
-/- :   S   N   L   R   Q   L   N   L   K   W   I   L   S   T   C   P   R   R   I   R   T   N   D   P
       TCC AAC CTG CGG CAG CTG AAC CTC AAG TGG ATT TTG TCC ACC TGT CCT CGA CGG ATC CGA ACA AAC GAC CCA
        87       90            96

120                          130
+/+ :  CAC ATG ACC ATT GAG CCC AGA ACC TTC CTG GCT ATG CGT ACA CTG GAG GAG CTG AAC CTG AGC TAT AAT GGT
        H   M   T   I   E   P   R   T   F   L   A   M   R   T   L   E   E   L   N   L   S   Y   N   G

-/- :   T   P   V   R   F   I   L   S   F   Y   C   R   S   P   Q   K   N   S   S   R   R   R   *
       ACA CCC GTG CGT TTT ATT CTG TCT TTT TAT TGC CGA TCC CCT CAG AAG AAC TCG TCA AGA AGG CGA TAG
```

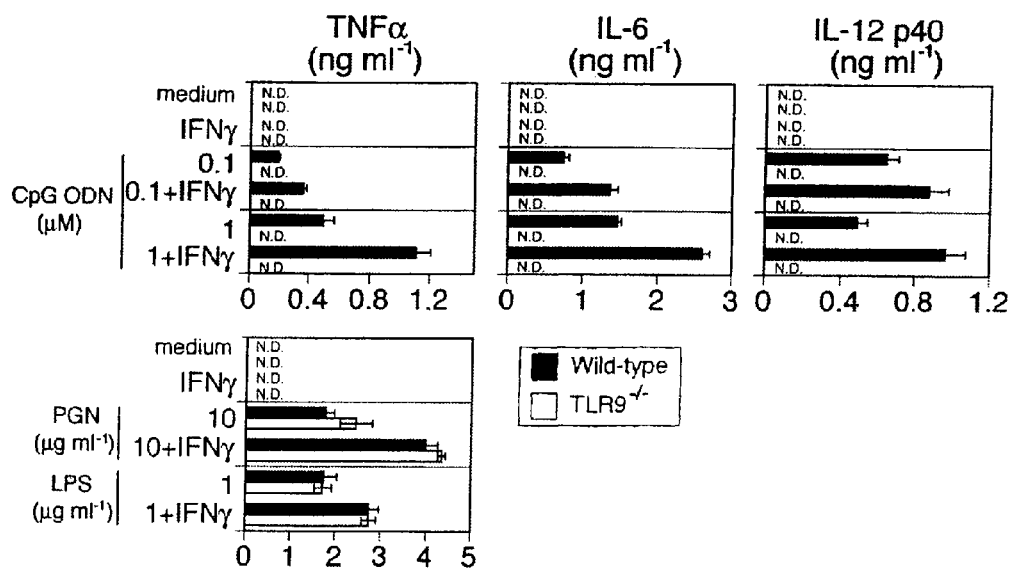

FIG. 5

SEQUENCE LISTING

```
<160> NUMBER OF SEQ ID NOS: 5

<210> SEQ ID NO 1
<211> LENGTH: 3257
<212> TYPE: DNA
<213> ORGANISM: Homo sapiens
<220> FEATURE:
<221> NAME/KEY: CDS
<222> LOCATION: (107)..(3205)

<400> SEQUENCE: 1
ccgctgctgc ccctgtggga agggacctcg agtgtgaagc atccttccct gtagctgctg         60
tccagtctgc ccgccagacc ctctggagaa gcccctgccc cccagc atg ggt ttc         115
                                                  Met Gly Phe
                                                   1 tgc cgc agc gcc ctg cac ccg ctg tct ctc ctg gtg cag gcc atc atg         163
Cys Arg Ser Ala Leu His Pro Leu Ser Leu Leu Val Gln Ala Ile Met
        5                  10                  15 ctg gcc atg acc ctg gcc ctg ggt acc ttg cct gcc ttc cta ccc tgt         211
Leu Ala Met Thr Leu Ala Leu Gly Thr Leu Pro Ala Phe Leu Pro Cys
```

-continued

```
            20                  25                  30                  35 gag ctc cag ccc cac ggc ctg gtg aac tgc aac tgg ctg ttc ctg aag        259
Glu Leu Gln Pro His Gly Leu Val Asn Cys Asn Trp Leu Phe Leu Lys
                    40                  45                  50 tct gtg ccc cac ttc tcc atg gca gca ccc cgt ggc aat gtc acc agc        307
Ser Val Pro His Phe Ser Met Ala Ala Pro Arg Gly Asn Val Thr Ser
                55                  60                  65 ctt tcc ttg tcc tcc aac cgc atc cac cac ctc cat gat tct gac ttt        355
Leu Ser Leu Ser Ser Asn Arg Ile His His Leu His Asp Ser Asp Phe
            70                  75                  80 gcc cac ctg ccc agc ctg cgg cat ctc aac ctc aag tgg aac tgc ccg        403
Ala His Leu Pro Ser Leu Arg His Leu Asn Leu Lys Trp Asn Cys Pro
        85                  90                  95 ccg gtt ggc ctc agc ccc atg cac ttc ccc tgc cac atg acc atc gag        451
Pro Val Gly Leu Ser Pro Met His Phe Pro Cys His Met Thr Ile Glu
100                 105                 110                 115 ccc agc acc ttc ttg gct gtg ccc acc ctg gaa gag cta aac ctg agc        499
Pro Ser Thr Phe Leu Ala Val Pro Thr Leu Glu Glu Leu Asn Leu Ser
                    120                 125                 130 tac aac aac atc atg act gtg cct gcg ctg ccc aaa tcc ctc ata tcc        547
Tyr Asn Asn Ile Met Thr Val Pro Ala Leu Pro Lys Ser Leu Ile Ser
                135                 140                 145 ctg tcc ctc agc cat acc aac atc ctg atg cta gac tct gcc agc ctc        595
Leu Ser Leu Ser His Thr Asn Ile Leu Met Leu Asp Ser Ala Ser Leu
            150                 155                 160 gcc ggc ctg cat gcc ctg cgc ttc cta ttc atg gac ggc aac tgt tat        643
Ala Gly Leu His Ala Leu Arg Phe Leu Phe Met Asp Gly Asn Cys Tyr
        165                 170                 175 tac aag aac ccc tgc agg cag gca ctg gag gtg gcc ccg ggt gcc ctc        691
Tyr Lys Asn Pro Cys Arg Gln Ala Leu Glu Val Ala Pro Gly Ala Leu
180                 185                 190                 195 ctt ggc ctg ggc aac ctc acc cac ctg tca ctc aag tac aac aac ctc        739
Leu Gly Leu Gly Asn Leu Thr His Leu Ser Leu Lys Tyr Asn Asn Leu
                    200                 205                 210 act gtg gtg ccc cgc aac ctg cct tcc agc ctg gag tat ctg ctg ttg        787
Thr Val Val Pro Arg Asn Leu Pro Ser Ser Leu Glu Tyr Leu Leu Leu
                215                 220                 225 tcc tac aac cgc atc gtc aaa ctg gcg cct gag gac ctg gcc aat ctg        835
Ser Tyr Asn Arg Ile Val Lys Leu Ala Pro Glu Asp Leu Ala Asn Leu
            230                 235                 240 acc gcc ctg cgt gtg ctc gat gtg ggc gga aat tgc cgc cgc tgc gac        883
Thr Ala Leu Arg Val Leu Asp Val Gly Gly Asn Cys Arg Arg Cys Asp
        245                 250                 255 cac gct ccc aac ccc tgc atg gag tgc cct cgt cac ttc ccc cag cta        931
His Ala Pro Asn Pro Cys Met Glu Cys Pro Arg His Phe Pro Gln Leu
260                 265                 270                 275 cat ccc gat acc ttc agc cac ctg agc cgt ctt gaa ggc ctg gtg ttg        979
His Pro Asp Thr Phe Ser His Leu Ser Arg Leu Glu Gly Leu Val Leu
                    280                 285                 290 aag gac agt tct ctc tcc tgg ctg aat gcc agt tgg ttc cgt ggg ctg       1027
Lys Asp Ser Ser Leu Ser Trp Leu Asn Ala Ser Trp Phe Arg Gly Leu
                295                 300                 305 gga aac ctc cga gtg ctg gac ctg agt gag aac ttc ctc tac aaa tgc       1075
Gly Asn Leu Arg Val Leu Asp Leu Ser Glu Asn Phe Leu Tyr Lys Cys
            310                 315                 320 atc act aaa acc aag gcc ttc cag ggc cta aca cag ctg cgc aag ctt       1123
Ile Thr Lys Thr Lys Ala Phe Gln Gly Leu Thr Gln Leu Arg Lys Leu
        325                 330                 335 aac ctg tcc ttc aat tac caa aag agg gtg tcc ttt gcc cac ctg tct       1171
```

```
                Asn Leu Ser Phe Asn Tyr Gln Lys Arg Val Ser Phe Ala His Leu Ser
                340                 345                 350                 355 ctg gcc cct tcc ttc ggg agc ctg gtc gcc ctg aag gag ctg gac atg          1219
Leu Ala Pro Ser Phe Gly Ser Leu Val Ala Leu Lys Glu Leu Asp Met
                    360                 365                 370 cac ggc atc ttc ttc cgc tca ctc gat gag acc acg ctc cgg cca ctg          1267
His Gly Ile Phe Phe Arg Ser Leu Asp Glu Thr Thr Leu Arg Pro Leu
                375                 380                 385 gcc cgc ctg ccc atg ctc cag act ctg cgt ctg cag atg aac ttc atc          1315
Ala Arg Leu Pro Met Leu Gln Thr Leu Arg Leu Gln Met Asn Phe Ile
            390                 395                 400 aac cag gcc cag ctc ggc atc ttc agg gcc ttc cct ggc ctg cgc tac          1363
Asn Gln Ala Gln Leu Gly Ile Phe Arg Ala Phe Pro Gly Leu Arg Tyr
        405                 410                 415 gtg gac ctg tcg gac aac cgc atc agc gga gct tcg gag ctg aca gcc          1411
Val Asp Leu Ser Asp Asn Arg Ile Ser Gly Ala Ser Glu Leu Thr Ala
420                 425                 430                 435 acc atg ggg gag gca gat gga ggg gag aag gtc tgg ctg cag cct ggg          1459
Thr Met Gly Glu Ala Asp Gly Gly Glu Lys Val Trp Leu Gln Pro Gly
                    440                 445                 450 gac ctt gct ccg gcc cca gtg gac act ccc agc tct gaa gac ttc agg          1507
Asp Leu Ala Pro Ala Pro Val Asp Thr Pro Ser Ser Glu Asp Phe Arg
                455                 460                 465 ccc aac tgc agc acc ctc aac ttc acc ttg gat ctg tca cgg aac aac          1555
Pro Asn Cys Ser Thr Leu Asn Phe Thr Leu Asp Leu Ser Arg Asn Asn
            470                 475                 480 ctg gtg acc gtg cag ccg gag atg ttt gcc cag ctc tcg cac ctg cag          1603
Leu Val Thr Val Gln Pro Glu Met Phe Ala Gln Leu Ser His Leu Gln
        485                 490                 495 tgc ctg cgc ctg agc cac aac tgc atc tcg cag gca gtc aat ggc tcc          1651
Cys Leu Arg Leu Ser His Asn Cys Ile Ser Gln Ala Val Asn Gly Ser
500                 505                 510                 515 cag ttc ctg ccg ctg acc ggt ctg cag gtg cta gac ctg tcc cac aat          1699
Gln Phe Leu Pro Leu Thr Gly Leu Gln Val Leu Asp Leu Ser His Asn
                    520                 525                 530 aag ctg gac ctc tac cac gag cac tca ttc acg gag cta cca cga ctg          1747
Lys Leu Asp Leu Tyr His Glu His Ser Phe Thr Glu Leu Pro Arg Leu
                535                 540                 545 gag gcc ctg gac ctc agc tac aac agc cag ccc ttt ggc atg cag ggc          1795
Glu Ala Leu Asp Leu Ser Tyr Asn Ser Gln Pro Phe Gly Met Gln Gly
            550                 555                 560 gtg ggc cac aac ttc agc ttc gtg gct cac ctg cgc acc ctg cgc cac          1843
Val Gly His Asn Phe Ser Phe Val Ala His Leu Arg Thr Leu Arg His
        565                 570                 575 ctc agc ctg gcc cac aac aac atc cac agc caa gtg tcc cag cag ctc          1891
Leu Ser Leu Ala His Asn Asn Ile His Ser Gln Val Ser Gln Gln Leu
580                 585                 590                 595 tgc agt acg tcg ctg cgg gcc ctg gac ttc agc ggc aat gca ctg ggc          1939
Cys Ser Thr Ser Leu Arg Ala Leu Asp Phe Ser Gly Asn Ala Leu Gly
                    600                 605                 610 cat atg tgg gcc gag gga gac ctc tat ctg cac ttc ttc caa ggc ctg          1987
His Met Trp Ala Glu Gly Asp Leu Tyr Leu His Phe Phe Gln Gly Leu
                615                 620                 625 agc ggt ttg atc tgg ctg gac ttg tcc cag aac cgc ctg cac acc ctc          2035
Ser Gly Leu Ile Trp Leu Asp Leu Ser Gln Asn Arg Leu His Thr Leu
            630                 635                 640 ctg ccc caa acc ctg cgc aac ctc ccc aag agc cta cag gtg ctg cgt          2083
Leu Pro Gln Thr Leu Arg Asn Leu Pro Lys Ser Leu Gln Val Leu Arg
        645                 650                 655
```

```
ctc cgt gac aat tac ctg gcc ttc ttt aag tgg tgg agc ctc cac ttc       2131
Leu Arg Asp Asn Tyr Leu Ala Phe Phe Lys Trp Trp Ser Leu His Phe
660                 665                 670                 675 ctg ccc aaa ctg gaa gtc ctc gac ctg gca gga aac cag ctg aag gcc       2179
Leu Pro Lys Leu Glu Val Leu Asp Leu Ala Gly Asn Gln Leu Lys Ala
            680                 685                 690 ctg acc aat ggc agc ctg cct gct ggc acc cgg ctc cgg agg ctg gat       2227
Leu Thr Asn Gly Ser Leu Pro Ala Gly Thr Arg Leu Arg Arg Leu Asp
                695                 700                 705 gtc agc tgc aac agc atc agc ttc gtg gcc ccc ggc ttc ttt tcc aag       2275
Val Ser Cys Asn Ser Ile Ser Phe Val Ala Pro Gly Phe Phe Ser Lys
710                 715                 720 gcc aag gag ctg cga gag ctc aac ctt agc gcc aac gcc ctc aag aca       2323
Ala Lys Glu Leu Arg Glu Leu Asn Leu Ser Ala Asn Ala Leu Lys Thr
725                 730                 735 gtg gac cac tcc tgg ttt ggg ccc ctg gcg agt gcc ctg caa ata cta       2371
Val Asp His Ser Trp Phe Gly Pro Leu Ala Ser Ala Leu Gln Ile Leu
740                 745                 750                 755 gat gta agc gcc aac cct ctg cac tgc gcc tgt ggg gcg gcc ttt atg       2419
Asp Val Ser Ala Asn Pro Leu His Cys Ala Cys Gly Ala Ala Phe Met
                760                 765                 770 gac ttc ctg ctg gag gtg cag gct gcc gtg ccc ggt ctg ccc agc cgg       2467
Asp Phe Leu Leu Glu Val Gln Ala Ala Val Pro Gly Leu Pro Ser Arg
                775                 780                 785 gtg aag tgt ggc agt ccg ggc cag ctc cag ggc ctc agc atc ttt gca       2515
Val Lys Cys Gly Ser Pro Gly Gln Leu Gln Gly Leu Ser Ile Phe Ala
            790                 795                 800 cag gac ctg cgc ctc tgc ctg gat gag gcc ctc tcc tgg gac tgt ttc       2563
Gln Asp Leu Arg Leu Cys Leu Asp Glu Ala Leu Ser Trp Asp Cys Phe
805                 810                 815 gcc ctc tcg ctg ctg gct gtg gct ctg ggc ctg ggt gtg ccc atg ctg       2611
Ala Leu Ser Leu Leu Ala Val Ala Leu Gly Leu Gly Val Pro Met Leu
820                 825                 830                 835 cat cac ctc tgt ggc tgg gac ctc tgg tac tgc ttc cac ctg tgc ctg       2659
His His Leu Cys Gly Trp Asp Leu Trp Tyr Cys Phe His Leu Cys Leu
                840                 845                 850 gcc tgg ctt ccc tgg cgg ggg cgg caa agt ggg cga gat gag gat gcc       2707
Ala Trp Leu Pro Trp Arg Gly Arg Gln Ser Gly Arg Asp Glu Asp Ala
            855                 860                 865 ctg ccc tac gat gcc ttc gtg gtc ttc gac aaa acg cag agc gca gtg       2755
Leu Pro Tyr Asp Ala Phe Val Val Phe Asp Lys Thr Gln Ser Ala Val
        870                 875                 880 gca gac tgg gtg tac aac gag ctt cgg ggg cag ctg gag gag tgc cgt       2803
Ala Asp Trp Val Tyr Asn Glu Leu Arg Gly Gln Leu Glu Glu Cys Arg
885                 890                 895 ggg cgc tgg gca ctc cgc ctg tgc ctg gag gaa cgc gac tgg ctg cct       2851
Gly Arg Trp Ala Leu Arg Leu Cys Leu Glu Glu Arg Asp Trp Leu Pro
900                 905                 910                 915 ggc aaa acc ctc ttt gag aac ctg tgg gcc tcg gtc tat ggc agc cgc       2899
Gly Lys Thr Leu Phe Glu Asn Leu Trp Ala Ser Val Tyr Gly Ser Arg
                920                 925                 930 aag acg ctg ttt gtg ctg gcc cac acg gac cgg gtc agt ggt ctc ttg       2947
Lys Thr Leu Phe Val Leu Ala His Thr Asp Arg Val Ser Gly Leu Leu
            935                 940                 945 cgc gcc agc ttc ctg ctg gcc cag cag cgc ctg ctg gag gac cgc aag       2995
Arg Ala Ser Phe Leu Leu Ala Gln Gln Arg Leu Leu Glu Asp Arg Lys
        950                 955                 960 gac gtc gtg gtg ctg gtg atc ctg agc cct gac ggc cgc cgc tcc cgc       3043
Asp Val Val Val Leu Val Ile Leu Ser Pro Asp Gly Arg Arg Ser Arg
965                 970                 975
```

```
tac gtg cgg ctg cgc cag cgc ctc tgc cgc cag agt gtc ctc ctc tgg      3091
Tyr Val Arg Leu Arg Gln Arg Leu Cys Arg Gln Ser Val Leu Leu Trp
980             985                 990                 995 ccc cac cag ccc agt ggt cag cgc agc ttc tgg gcc cag ctg ggc atg      3139
Pro His Gln Pro Ser Gly Gln Arg Ser Phe Trp Ala Gln Leu Gly Met
            1000                1005                1010 gcc ctg acc agg gac aac cac cac ttc tat aac cgg aac ttc tgc cag      3187
Ala Leu Thr Arg Asp Asn His His Phe Tyr Asn Arg Asn Phe Cys Gln
        1015                1020                1025 gga ccc acg gcc gaa tag ccgtgagccg gaatcctgca cggtgccacc              3235
Gly Pro Thr Ala Glu
        1030 tccacactca cctcacctct gc                                              3257

<210> SEQ ID NO 2
<211> LENGTH: 1032
<212> TYPE: PRT
<213> ORGANISM: Homo sapiens

<400> SEQUENCE: 2

Met Gly Phe Cys Arg Ser Ala Leu His Pro Leu Ser Leu Leu Val Gln
 1               5                  10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
        35                  40                  45

Phe Leu Lys Ser Val Pro His Phe Ser Met Ala Ala Pro Arg Gly Asn
    50                  55                  60

Val Thr Ser Leu Ser Leu Ser Ser Asn Arg Ile His His Leu His Asp
 65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110

Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
    130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
            180                 185                 190

Gly Ala Leu Leu Gly Leu Gly Asn Leu Thr His Leu Ser Leu Lys Tyr
        195                 200                 205

Asn Asn Leu Thr Val Val Pro Arg Asn Leu Pro Ser Ser Leu Glu Tyr
    210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
            260                 265                 270

Pro Gln Leu His Pro Asp Thr Phe Ser His Leu Ser Arg Leu Glu Gly
```

```
            275                 280                 285
Leu Val Leu Lys Asp Ser Ser Leu Ser Trp Leu Asn Ala Ser Trp Phe
290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
                340                 345                 350

His Leu Ser Leu Ala Pro Ser Phe Gly Ser Leu Val Ala Leu Lys Glu
                355                 360                 365

Leu Asp Met His Gly Ile Phe Phe Arg Ser Leu Asp Glu Thr Thr Leu
370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
                420                 425                 430

Leu Thr Ala Thr Met Gly Glu Ala Asp Gly Gly Glu Lys Val Trp Leu
                435                 440                 445

Gln Pro Gly Asp Leu Ala Pro Ala Pro Val Asp Thr Pro Ser Ser Glu
450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
                500                 505                 510

Asn Gly Ser Gln Phe Leu Pro Leu Thr Gly Leu Gln Val Leu Asp Leu
                515                 520                 525

Ser His Asn Lys Leu Asp Leu Tyr His Glu His Ser Phe Thr Glu Leu
530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
                580                 585                 590

Gln Gln Leu Cys Ser Thr Ser Leu Arg Ala Leu Asp Phe Ser Gly Asn
                595                 600                 605

Ala Leu Gly His Met Trp Ala Glu Gly Asp Leu Tyr Leu His Phe Phe
610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
                660                 665                 670

Leu His Phe Leu Pro Lys Leu Glu Val Leu Asp Leu Ala Gly Asn Gln
                675                 680                 685

Leu Lys Ala Leu Thr Asn Gly Ser Leu Pro Ala Gly Thr Arg Leu Arg
690                 695                 700
```

-continued

```
Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
        835                 840                 845

Leu Cys Leu Ala Trp Leu Pro Trp Arg Gly Arg Gln Ser Gly Arg Asp
    850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
    930                 935                 940

Gly Leu Leu Arg Ala Ser Phe Leu Leu Ala Gln Gln Arg Leu Leu Glu
945                 950                 955                 960

Asp Arg Lys Asp Val Val Val Leu Val Ile Leu Ser Pro Asp Gly Arg
                965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
        995                 1000                1005

Leu Gly Met Ala Leu Thr Arg Asp Asn His His Phe Tyr Asn Arg Asn
    1010                1015                1020

Phe Cys Gln Gly Pro Thr Ala Glu
1025                1030

<210> SEQ ID NO 3
<211> LENGTH: 3471
<212> TYPE: DNA
<213> ORGANISM: Mus musculus
<220> FEATURE:
<221> NAME/KEY: CDS
<222> LOCATION: (107)..(3205)

<400> SEQUENCE: 3
tgaaagtgtc acttcctcaa ttctctgaga gaccctggtg tggaacatca ttctctgccg      60
cccagtttgt cagagggagc ctcgggagaa tcctccatct cccaac atg gtt ctc       115
                                                  Met Val Leu
```

```
                                                        1
cgt cga agg act ctg cac ccc ttg tcc ctc ctg gta cag gct gca gtg     163
Arg Arg Arg Thr Leu His Pro Leu Ser Leu Leu Val Gln Ala Ala Val
        5                   10                  15 ctg gct gag act ctg gcc ctg ggt acc ctg cct gcc ttc cta ccc tgt     211
Leu Ala Glu Thr Leu Ala Leu Gly Thr Leu Pro Ala Phe Leu Pro Cys
 20              25                  30                  35 gag ctg aag cct cat ggc ctg gtg gac tgc aat tgg ctg ttc ctg aag     259
Glu Leu Lys Pro His Gly Leu Val Asp Cys Asn Trp Leu Phe Leu Lys
                 40                  45                  50 tct gta ccc cgt ttc tct gcg gca gca tcc tgc tcc aac atc acc cgc     307
Ser Val Pro Arg Phe Ser Ala Ala Ala Ser Cys Ser Asn Ile Thr Arg
             55                  60                  65 ctc tcc ttg atc tcc aac cgt atc cac cac ctg cac aac tcc gac ttc     355
Leu Ser Leu Ile Ser Asn Arg Ile His His Leu His Asn Ser Asp Phe
         70                  75                  80 gtc cac ctg tcc aac ctg cgg cag ctg aac ctc aag tgg aac tgt cca     403
Val His Leu Ser Asn Leu Arg Gln Leu Asn Leu Lys Trp Asn Cys Pro
     85                  90                  95 ccc act ggc ctt agc ccc ttg cac ttc tct tgc cac atg acc att gag     451
Pro Thr Gly Leu Ser Pro Leu His Phe Ser Cys His Met Thr Ile Glu
100                 105                 110                 115 ccc aga acc ttc ctg gct atg cgt aca ctg gag gag ctg aac ctg agc     499
Pro Arg Thr Phe Leu Ala Met Arg Thr Leu Glu Glu Leu Asn Leu Ser
                120                 125                 130 tat aat ggt atc acc act gtg ccc cga ctg ccc agc tcc ctg gtg aat     547
Tyr Asn Gly Ile Thr Thr Val Pro Arg Leu Pro Ser Ser Leu Val Asn
            135                 140                 145 ctg agc ctg agc cac acc aac atc ctg gtt cta gat gct aac agc ctc     595
Leu Ser Leu Ser His Thr Asn Ile Leu Val Leu Asp Ala Asn Ser Leu
        150                 155                 160 gcc ggc cta tac agc ctg cgc gtt ctc ttc atg gac ggg aac tgc tac     643
Ala Gly Leu Tyr Ser Leu Arg Val Leu Phe Met Asp Gly Asn Cys Tyr
    165                 170                 175 tac aag aac ccc tgc aca gga gcg gtg aag gtg acc cca ggc gcc ctc     691
Tyr Lys Asn Pro Cys Thr Gly Ala Val Lys Val Thr Pro Gly Ala Leu
180                 185                 190                 195 ctg ggc ctg agc aat ctc acc cat ctg tct gtg aag tat aac aac ctc     739
Leu Gly Leu Ser Asn Leu Thr His Leu Ser Val Lys Tyr Asn Asn Leu
                200                 205                 210 aca aag gtg ccc cgc caa ctg ccc ccc agc ctg gag tac ctc ctg gtg     787
Thr Lys Val Pro Arg Gln Leu Pro Pro Ser Leu Glu Tyr Leu Leu Val
            215                 220                 225 tcc tat aac ctc att gtc aag ctg ggg cct gaa gac ctg gcc aat ctg     835
Ser Tyr Asn Leu Ile Val Lys Leu Gly Pro Glu Asp Leu Ala Asn Leu
        230                 235                 240 acc tcc ctt cga gta ctt gat gtg ggt ggg aat tgc gtc gcc tgc gac     883
Thr Ser Leu Arg Val Leu Asp Val Gly Gly Asn Cys Arg Arg Cys Asp
    245                 250                 255 cat gcc ccc aat ccc tgt ata gaa tgt ggc caa aag tcc ctc cac ctg     931
His Ala Pro Asn Pro Cys Ile Glu Cys Gly Gln Lys Ser Leu His Leu
260                 265                 270                 275 cac cct gag acc ttc cat cac ctg agc cat ctg gaa ggc ctg gtg ctg     979
His Pro Glu Thr Phe His His Leu Ser His Leu Glu Gly Leu Val Leu
                280                 285                 290 aag gac agc tct ctc cat aca ctg aac tct tcc tgg ttc caa ggt ctg     1027
Lys Asp Ser Ser Leu His Thr Leu Asn Ser Ser Trp Phe Gln Gly Leu
            295                 300                 305 gtc aac ctc tcg gtg ctg gac cta agc gag aac ttt ctc tat gaa agc     1075
```

```
        Val Asn Leu Ser Val Leu Asp Leu Ser Glu Asn Phe Leu Tyr Glu Ser
                310             315                 320 atc aac cac acc aat gcc ttt cag aac cta acc cgc ctg cgc aag ctc       1123
Ile Asn His Thr Asn Ala Phe Gln Asn Leu Thr Arg Leu Arg Lys Leu
325                 330                 335 aac ctg tcc ttc aat tac cgc aag aag gta tcc ttt gcc cgc ctc cac       1171
Asn Leu Ser Phe Asn Tyr Arg Lys Lys Val Ser Phe Ala Arg Leu His
340                 345                 350                 355 ctg gca agt tcc ttc aag aac ctg gtg tca ctg cag gag ctg aac atg       1219
Leu Ala Ser Ser Phe Lys Asn Leu Val Ser Leu Gln Glu Leu Asn Met
                360                 365                 370 aac ggc atc ttc ttc cgc tcg ctc aac aag tac acg ctc aga tgg ctg       1267
Asn Gly Ile Phe Phe Arg Ser Leu Asn Lys Tyr Thr Leu Arg Trp Leu
                375                 380                 385 gcc gat ctg ccc aaa ctc cac act ctg cat ctt caa atg aac ttc atc       1315
Ala Asp Leu Pro Lys Leu His Thr Leu His Leu Gln Met Asn Phe Ile
            390                 395                 400 aac cag gca cag ctc agc atc ttt ggt acc ttc cga gcc ctt cgc ttt       1363
Asn Gln Ala Gln Leu Ser Ile Phe Gly Thr Phe Arg Ala Leu Arg Phe
            405                 410                 415 gtg gac ttg tca gac aat cgc atc agt ggg cct tca acg ctg tca gaa       1411
Val Asp Leu Ser Asp Asn Arg Ile Ser Gly Pro Ser Thr Leu Ser Glu
420                 425                 430                 435 gcc acc cct gaa gag gca gat gat gca gag cag gag gag ctg ttg tct       1459
Ala Thr Pro Glu Glu Ala Asp Asp Ala Glu Gln Glu Glu Leu Leu Ser
                440                 445                 450 gcg gat cct cac cca gct cca ctg agc acc cct gct tct aag aac ttc       1507
Ala Asp Pro His Pro Ala Pro Leu Ser Thr Pro Ala Ser Lys Asn Phe
            455                 460                 465 atg gac agg tgt aag aac ttc aag ttc acc atg gac ctg tct cgg aac       1555
Met Asp Arg Cys Lys Asn Phe Lys Phe Thr Met Asp Leu Ser Arg Asn
            470                 475                 480 aac ctg gtg act atc aag cca gag atg ttt gtc aat ctc tca cgc ctc       1603
Asn Leu Val Thr Ile Lys Pro Glu Met Phe Val Asn Leu Ser Arg Leu
        485                 490                 495 cag tgt ctt agc ctg agc cac aac tcc att gca cag gct gtc aat ggc       1651
Gln Cys Leu Ser Leu Ser His Asn Ser Ile Ala Gln Ala Val Asn Gly
500                 505                 510                 515 tct cag ttc ctg ccg ctg act aat ctg cag gtg ctg gac ctg tcc cat       1699
Ser Gln Phe Leu Pro Leu Thr Asn Leu Gln Val Leu Asp Leu Ser His
                520                 525                 530 aac aaa ctg gac ttg tac cac tgg aaa tcg ttc agt gag cta cca cag       1747
Asn Lys Leu Asp Leu Tyr His Trp Lys Ser Phe Ser Glu Leu Pro Gln
            535                 540                 545 ttg cag gcc ctg gac ctg agc tac aac agc cag ccc ttt agc atg aag       1795
Leu Gln Ala Leu Asp Leu Ser Tyr Asn Ser Gln Pro Phe Ser Met Lys
        550                 555                 560 ggt ata ggc cac aat ttc agt ttt gtg gcc cat ctg tcc atg cta cac       1843
Gly Ile Gly His Asn Phe Ser Phe Val Ala His Leu Ser Met Leu His
565                 570                 575 agc ctt agc ctg gca cac aat gac att cat acc cgt gtg tcc tca cat       1891
Ser Leu Ser Leu Ala His Asn Asp Ile His Thr Arg Val Ser Ser His
580                 585                 590                 595 ctc aac agc aac tca gtg agg ttt ctt gac ttc agc ggc aac ggt atg       1939
Leu Asn Ser Asn Ser Val Arg Phe Leu Asp Phe Ser Gly Asn Gly Met
                600                 605                 610 ggc cgc atg tgg gat gag ggg ggc ctt tat ctc cat ttc ttc caa ggc       1987
Gly Arg Met Trp Asp Glu Gly Gly Leu Tyr Leu His Phe Phe Gln Gly
            615                 620                 625
```

```
ctg agt ggc ctg ctg aag ctg gac ctg tct caa aat aac ctg cat atc      2035
Leu Ser Gly Leu Leu Lys Leu Asp Leu Ser Gln Asn Asn Leu His Ile
        630                 635                 640 ctc cgg ccc cag aac ctt gac aac ctc ccc aag agc ctg aag ctg ctg      2083
Leu Arg Pro Gln Asn Leu Asp Asn Leu Pro Lys Ser Leu Lys Leu Leu
    645                 650                 655 agc ctc cga gac aac tac cta tct ttc ttt aac tgg acc agt ctg tcc      2131
Ser Leu Arg Asp Asn Tyr Leu Ser Phe Phe Asn Trp Thr Ser Leu Ser
660                 665                 670                 675 ttc ctg ccc aac ctg gaa gtc cta gac ctg gca ggc aac cag cta aag      2179
Phe Leu Pro Asn Leu Glu Val Leu Asp Leu Ala Gly Asn Gln Leu Lys
                680                 685                 690 gcc ctg acc aat ggc acc ctg cct aat ggc acc ctc ctc cag aaa ctg      2227
Ala Leu Thr Asn Gly Thr Leu Pro Asn Gly Thr Leu Leu Gln Lys Leu
    695                 700                 705 gat gtc agc agc aac agt atc gtc tct gtg gtc cca gcc ttc ttc gct      2275
Asp Val Ser Ser Asn Ser Ile Val Ser Val Val Pro Ala Phe Phe Ala
710                 715                 720 ctg gcg gtc gag ctg aaa gag gtc aac ctc agc cac aac att ctc aag      2323
Leu Ala Val Glu Leu Lys Glu Val Asn Leu Ser His Asn Ile Leu Lys
                725                 730                 735 acg gtg gat cgc tcc tgg ttt ggg ccc att gtg atg aac ctg aca gtt      2371
Thr Val Asp Arg Ser Trp Phe Gly Pro Ile Val Met Asn Leu Thr Val
740                 745                 750                 755 cta gac gtg aga agc aac cct ctg cac tgt gcc tgt ggg gca gcc ttc      2419
Leu Asp Val Arg Ser Asn Pro Leu His Cys Ala Cys Gly Ala Ala Phe
                760                 765                 770 gta gac tta ctg ttg gag gtg cag acc aag gtg cct ggc ctg gct aat      2467
Val Asp Leu Leu Leu Glu Val Gln Thr Lys Val Pro Gly Leu Ala Asn
    775                 780                 785 ggt gtg aag tgt ggc agc ccc ggc cag ctg cag ggc cgt agc atc ttc      2515
Gly Val Lys Cys Gly Ser Pro Gly Gln Leu Gln Gly Arg Ser Ile Phe
790                 795                 800 gca cag gac ctg cgg ctg tgc ctg gat gag gtc ctc tct tgg gac tgc      2563
Ala Gln Asp Leu Arg Leu Cys Leu Asp Glu Val Leu Ser Trp Asp Cys
    805                 810                 815 ttt ggc ctt tca ctc ttg gct gtg gcc gtg ggc atg gtg gtg cct ata      2611
Phe Gly Leu Ser Leu Leu Ala Val Ala Val Gly Met Val Val Pro Ile
820                 825                 830                 835 ctg cac cat ctc tgc ggc tgg gac gtc tgg tac tgt ttt cat ctg tgc      2659
Leu His His Leu Cys Gly Trp Asp Val Trp Tyr Cys Phe His Leu Cys
                840                 845                 850 ctg gca tgg cta cct ttg ctg gcc cgc agc cga cgc agc gcc caa gct      2707
Leu Ala Trp Leu Pro Leu Leu Ala Arg Ser Arg Arg Ser Ala Gln Ala
    855                 860                 865 ctc ccc tat gat gcc ttc gtg gtg ttc gat aag gca cag agc gca gtt      2755
Leu Pro Tyr Asp Ala Phe Val Val Phe Asp Lys Ala Gln Ser Ala Val
870                 875                 880 gcg gac tgg gtg tat aac gag ctg cgg gtg cgg ctg gag gag cgg cgc      2803
Ala Asp Trp Val Tyr Asn Glu Leu Arg Val Arg Leu Glu Glu Arg Arg
    885                 890                 895 ggt cgc cga gcc cta cgc ttg tgt ctg gag gac cga gat tgg ctg cct      2851
Gly Arg Arg Ala Leu Arg Leu Cys Leu Glu Asp Arg Asp Trp Leu Pro
900                 905                 910                 915 ggc cag acg ctc ttc gag aac ctc tgg gct tcc atc tat ggg agc cgc      2899
Gly Gln Thr Leu Phe Glu Asn Leu Trp Ala Ser Ile Tyr Gly Ser Arg
                920                 925                 930 aag act cta ttt gtg ctg gcc cac acg gac cgc gtc agt ggc ctc ctg      2947
Lys Thr Leu Phe Val Leu Ala His Thr Asp Arg Val Ser Gly Leu Leu
    935                 940                 945
```

-continued

```
cgc acc agc ttc ctg ctg gct cag cag cgc ctg ttg gaa gac cgc aag       2995
Arg Thr Ser Phe Leu Leu Ala Gln Gln Arg Leu Leu Glu Asp Arg Lys
        950                 955                 960 gac gtg gtg gtg ttg gtg atc ctg cgt ccg gat gcc cac cgc tcc cgc       3043
Asp Val Val Val Leu Val Ile Leu Arg Pro Asp Ala His Arg Ser Arg
965                 970                 975 tat gtg cga ctg cgc cag cgt ctc tgc cgc cag agt gtg ctc ttc tgg       3091
Tyr Val Arg Leu Arg Gln Arg Leu Cys Arg Gln Ser Val Leu Phe Trp
980                 985                 990                 995 ccc cag cag ccc aac ggg cag ggg ggc ttc tgg gcc cag ctg agt aca       3139
Pro Gln Gln Pro Asn Gly Gln Gly Gly Phe Trp Ala Gln Leu Ser Thr
            1000                1005                1010 gcc ctg act agg gac aac cgc cac ttc tat aac cag aac ttc tgc cgg       3187
Ala Leu Thr Arg Asp Asn Arg His Phe Tyr Asn Gln Asn Phe Cys Arg
        1015                1020                1025 gga cct aca gca gaa tag ctcagagcaa cagctggaaa cagctgcatc              3235
Gly Pro Thr Ala Glu
        1030 ttcatgcctg gttcccgagt tgctctgcct gccttgctct gtcttactac accgctattt    3295 ggcaagtgcg caatatatgc taccaagcca ccaggcccac ggagcaaagg ttggcagtaa    3355 agggtagttt tcttcccatg catctttcag gagagtgaag atagacacca gacccacaca    3415 gaacaggact ggagttcatt ctctgcccct ccaccccact ttgcctgtct ctgtat        3471

<210> SEQ ID NO 4
<211> LENGTH: 1032
<212> TYPE: PRT
<213> ORGANISM: Mus musculus

<400> SEQUENCE: 4

Met Val Leu Arg Arg Thr Leu His Pro Leu Ser Leu Leu Val Gln
1               5                   10                  15

Ala Ala Val Leu Ala Glu Thr Leu Ala Leu Gly Thr Leu Pro Ala Phe
            20                  25                  30

Leu Pro Cys Glu Leu Lys Pro His Gly Leu Val Asp Cys Asn Trp Leu
        35                  40                  45

Phe Leu Lys Ser Val Pro Arg Phe Ser Ala Ala Ala Ser Cys Ser Asn
    50                  55                  60

Ile Thr Arg Leu Ser Leu Ile Ser Asn Arg Ile His His Leu His Asn
65                  70                  75                  80

Ser Asp Phe Val His Leu Ser Asn Leu Arg Gln Leu Asn Leu Lys Trp
                85                  90                  95

Asn Cys Pro Pro Thr Gly Leu Ser Pro Leu His Phe Ser Cys His Met
            100                 105                 110

Thr Ile Glu Pro Arg Thr Phe Leu Ala Met Arg Thr Leu Glu Glu Leu
        115                 120                 125

Asn Leu Ser Tyr Asn Gly Ile Thr Thr Val Pro Arg Leu Pro Ser Ser
    130                 135                 140

Leu Val Asn Leu Ser Leu Ser His Thr Asn Ile Leu Val Leu Asp Ala
145                 150                 155                 160

Asn Ser Leu Ala Gly Leu Tyr Ser Leu Arg Val Leu Phe Met Asp Gly
                165                 170                 175

Asn Cys Tyr Tyr Lys Asn Pro Cys Thr Gly Ala Val Lys Val Thr Pro
            180                 185                 190

Gly Ala Leu Leu Gly Leu Ser Asn Leu Thr His Leu Ser Val Lys Tyr
        195                 200                 205
```

```
Asn Asn Leu Thr Lys Val Pro Arg Gln Leu Pro Pro Ser Leu Glu Tyr
    210                 215                 220
Leu Leu Val Ser Tyr Asn Leu Ile Val Lys Leu Gly Pro Glu Asp Leu
225                 230                 235                 240
Ala Asn Leu Thr Ser Leu Arg Val Leu Asp Val Gly Gly Asn Cys Arg
                245                 250                 255
Arg Cys Asp His Ala Pro Asn Pro Cys Ile Glu Cys Gly Gln Lys Ser
            260                 265                 270
Leu His Leu His Pro Glu Thr Phe His His Leu Ser His Leu Glu Gly
        275                 280                 285
Leu Val Leu Lys Asp Ser Ser Leu His Thr Leu Asn Ser Ser Trp Phe
    290                 295                 300
Gln Gly Leu Val Asn Leu Ser Val Leu Asp Leu Ser Glu Asn Phe Leu
305                 310                 315                 320
Tyr Glu Ser Ile Asn His Thr Asn Ala Phe Gln Asn Leu Thr Arg Leu
                325                 330                 335
Arg Lys Leu Asn Leu Ser Phe Asn Tyr Arg Lys Lys Val Ser Phe Ala
            340                 345                 350
Arg Leu His Leu Ala Ser Ser Phe Lys Asn Leu Val Ser Leu Gln Glu
        355                 360                 365
Leu Asn Met Asn Gly Ile Phe Phe Arg Ser Leu Asn Lys Tyr Thr Leu
    370                 375                 380
Arg Trp Leu Ala Asp Leu Pro Lys Leu His Thr Leu His Leu Gln Met
385                 390                 395                 400
Asn Phe Ile Asn Gln Ala Gln Leu Ser Ile Phe Gly Thr Phe Arg Ala
                405                 410                 415
Leu Arg Phe Val Asp Leu Ser Asp Asn Arg Ile Ser Gly Pro Ser Thr
            420                 425                 430
Leu Ser Glu Ala Thr Pro Glu Glu Ala Asp Asp Ala Glu Gln Glu Glu
        435                 440                 445
Leu Leu Ser Ala Asp Pro His Pro Ala Pro Leu Ser Thr Pro Ala Ser
    450                 455                 460
Lys Asn Phe Met Asp Arg Cys Lys Asn Phe Lys Phe Thr Met Asp Leu
465                 470                 475                 480
Ser Arg Asn Asn Leu Val Thr Ile Lys Pro Glu Met Phe Val Asn Leu
                485                 490                 495
Ser Arg Leu Gln Cys Leu Ser Leu Ser His Asn Ser Ile Ala Gln Ala
            500                 505                 510
Val Asn Gly Ser Gln Phe Leu Pro Leu Thr Asn Leu Gln Val Leu Asp
        515                 520                 525
Leu Ser His Asn Lys Leu Asp Leu Tyr His Trp Lys Ser Phe Ser Glu
    530                 535                 540
Leu Pro Gln Leu Gln Ala Leu Asp Leu Ser Tyr Asn Ser Gln Pro Phe
545                 550                 555                 560
Ser Met Lys Gly Ile Gly His Asn Phe Ser Phe Val Ala His Leu Ser
                565                 570                 575
Met Leu His Ser Leu Ser Leu Ala His Asn Asp Ile His Thr Arg Val
            580                 585                 590
Ser Ser His Leu Asn Ser Asn Ser Val Arg Phe Leu Asp Phe Ser Gly
        595                 600                 605
Asn Gly Met Gly Arg Met Trp Asp Glu Gly Gly Leu Tyr Leu His Phe
    610                 615                 620
```

-continued

```
Phe Gln Gly Leu Ser Gly Leu Leu Lys Leu Asp Leu Ser Gln Asn Asn
625                 630                 635                 640

Leu His Ile Leu Arg Pro Gln Asn Leu Asp Asn Leu Pro Lys Ser Leu
            645                 650                 655

Lys Leu Leu Ser Leu Arg Asp Asn Tyr Leu Ser Phe Phe Asn Trp Thr
        660                 665                 670

Ser Leu Ser Phe Leu Pro Asn Leu Glu Val Leu Asp Leu Ala Gly Asn
    675                 680                 685

Gln Leu Lys Ala Leu Thr Asn Gly Thr Leu Pro Asn Gly Thr Leu Leu
690                 695                 700

Gln Lys Leu Asp Val Ser Asn Ser Ile Val Ser Val Val Pro Ala
705                 710                 715                 720

Phe Phe Ala Leu Ala Val Glu Leu Lys Glu Val Asn Leu Ser His Asn
                725                 730                 735

Ile Leu Lys Thr Val Asp Arg Ser Trp Phe Gly Pro Ile Val Met Asn
            740                 745                 750

Leu Thr Val Leu Asp Val Arg Ser Asn Pro Leu His Cys Ala Cys Gly
        755                 760                 765

Ala Ala Phe Val Asp Leu Leu Leu Glu Val Gln Thr Lys Val Pro Gly
    770                 775                 780

Leu Ala Asn Gly Val Lys Cys Gly Ser Pro Gly Gln Leu Gln Gly Arg
785                 790                 795                 800

Ser Ile Phe Ala Gln Asp Leu Arg Leu Cys Leu Asp Glu Val Leu Ser
                805                 810                 815

Trp Asp Cys Phe Gly Leu Ser Leu Leu Ala Val Ala Val Gly Met Val
            820                 825                 830

Val Pro Ile Leu His His Leu Cys Gly Trp Asp Val Trp Tyr Cys Phe
        835                 840                 845

His Leu Cys Leu Ala Trp Leu Pro Leu Leu Ala Arg Ser Arg Arg Ser
    850                 855                 860

Ala Gln Ala Leu Pro Tyr Asp Ala Phe Val Val Phe Asp Lys Ala Gln
865                 870                 875                 880

Ser Ala Val Ala Asp Trp Val Tyr Asn Glu Leu Arg Val Arg Leu Glu
                885                 890                 895

Glu Arg Arg Gly Arg Arg Ala Leu Arg Leu Cys Leu Glu Asp Arg Asp
            900                 905                 910

Trp Leu Pro Gly Gln Thr Leu Phe Glu Asn Leu Trp Ala Ser Ile Tyr
        915                 920                 925

Gly Ser Arg Lys Thr Leu Phe Val Leu Ala His Thr Asp Arg Val Ser
    930                 935                 940

Gly Leu Leu Arg Thr Ser Phe Leu Leu Ala Gln Gln Arg Leu Leu Glu
945                 950                 955                 960

Asp Arg Lys Asp Val Val Val Leu Val Ile Leu Arg Pro Asp Ala His
                965                 970                 975

Arg Ser Arg Tyr Val Arg Leu Arg Gln Arg Leu Cys Arg Gln Ser Val
            980                 985                 990

Leu Phe Trp Pro Gln Gln Pro Asn Gly Gln Gly Phe Trp Ala Gln
        995                 1000                1005

Leu Ser Thr Ala Leu Thr Arg Asp Asn Arg His Phe Tyr Asn Gln Asn
    1010                1015                1020

Phe Cys Arg Gly Pro Thr Ala Glu
1025                1030
```

```
-continued

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:CpG ODN

<400> SEQUENCE: 5
tccatgacgt tcctgatgct                                               20
```

TRANSGENIC TOLL-LIKE RECEPTOR 9 (TLR9) MICE

This application is a 371 of International Application No. PCT/JP01/04731, filed Jun. 5, 2001, which claims priority to JP 2000-219652, filed Jul. 19, 2000, the contents of which are incorporated herein by reference.

TECHNICAL FIELD

The present invention relates to a receptor protein specifically recognizing bacterial DNA having an unmethylated CpG sequence, a gene of the receptor protein and uses of them.

BACKGROUND OF THE INVENTION

It is already known that Toll genes are necessary for determining the dorsoventral axis in the embryogeny of Dorsophilia (Cell 52, 269-279, 1988, Annu Rev. Cell Dev. Biol. 12, 393-416, 1996) and for antifungal immune responses in the adult fly (Cell 86, 973-983, 1996).

It has been shown that the Toll is a Type I transmembrane receptor comprising leucine-rich repeat (LRR) in extracellular domains, and its intracellular domains are highly homologous to the intracellular domains of mammalian interleukin-1 receptor (IL-1R) (Nature 351, 355-356, 1991, Annu. Rev. Cell Dev. Biol. 12, 393-416, 1996, J. Leukoc. Biol. 63, 650-657, 1998).

Recently, mammalian homologs of Toll called Toll-like Receptor (TLR) have been identified, and six members of the family such as TLR2 and TLR4 have been reported (Nature 388, 394-397, 1997, Proc. Natl. Acad. Sci. USA 95, 588-593, 1998, Blood 91, 4020-4027, 1998, Gene 231, 59-65, 1999). It is known that a member of the TLR family mediates MyD88, an adopter protein as IL-LR is, recruits IL-LR binding kinase (IRAK), activates TRAF6, and activates downstream NF-κB (J. Exp. Med. 187, 2097-2101, 1998, Mol. Cell 2, 253-258, 1998, Immunity 11, 115-122, 1999). It is also thought that the role of the TLR family in mammals is related to innate immune recognition as a pattern recognition receptor (PRR) recognizing bacterial common components (Cell 91, 295-298, 1997).

It is well known that one of the pathogen-associated molecular patterns (PAMP) recognized by the PRR mentioned above is lipopolysaccharide (LPS), which is a main component of the outer membrane of Gramm-negative bacteria (Cell 91, 295-298, 1997), the LPS stimulates a host cell to produce various inflammatory cytokines such as TNF α, IL-1 or IL-6 in the host cell (Adv. Immunol. 28, 293-450, 1979, Annu. Rev. Immunol. 13, 437-457, 1995), and the LPS captured by LPS-binding protein (LBP) is transferred to CD 14 on the surface of a cell (Science 249, 1431-1433, 1990, Annu. Rev. Immunol. 13, 437-457, 1995). The present inventors generated TLR4 knockout mice and reported that the TLR4 knockout mice lack the ability to respond to LPS, a main component of the outer membrane of the Gram-negative bacteria (J. Immunol. 162, 3749-3752, 1999), and also generated TLR2 knockout mice and reported that macrophages derived from TLR2 knockout mice showed low levels of response to cell wall of Gram-negative bacteria or peptidoglycan, a component of the Gram-negative bacteria (Immunity 11, 443-451, 1999).

On the other hand, from the fact that the oligonucleotides comprising bacterial DNA (DNA derived from bacteria) or an unmethylated CpG sequence stimulate immune cells of mice or human (Trends Microbiol. 4, 73-76, 1996, Trends Microbiol. 6, 496-500, 1998), and stimulate a T helper 1 cells (Th1)-like inflammatory response dominated by the release of IL-12 and IFNγ (EMBO J. 18, 6973-6982, 1999, J. Immunol. 161, 3042-3049, 1998, Proc. Natl. Acad. Sci. USA 96, 9305-9310, 1999), it is advocated that the oligonucleotides comprising CpG sequence are possibly used as an adjuvant in vaccine strategies including vaccines to cancer, allergy and infectious diseases (Adv. Immunol. 73, 329-368, 1999, Curr.Opin. Immunol. 12, 35-43, 2000, Immunity 11, 123-129, 1999). Although its effects have been expected in the clinical practice in this way, the molecular mechanism by which bacterial DNA comprising an unmethylated CpG sequence activates immune cells is unclear.

Although the DNA derived from bacteria comprising an unmethylated CpG motif activates immune cells significantly and induces response by Th1 as mentioned above, the activities at the molecular level are not well understood. The goal of the present invention is to provide a receptor protein TLR9, a member of TLR family specifically recognizing bacterial DNA comprising an unmethylated CpG sequence, the DNA encoding it, and the artificial animal models useful in examining response of host immune cells to bacterial infectious diseases, which elucidate effects of oligonucleotides comprising an unmethylated CpG sequence of bacterial DNA at the molecular level.

As a member of the mammalian TLR family, a pattern recognition receptor recognizing common structures of bacteria, relevant to innate immune recognition, six members (TLR1 to 6) have been publicized until now (Nature 388, 384-397, 1997, Proc. Natl. Acad. Sci. USA, 95, 588-593, 1998, Gene 231, 59-65, 1999), and TLR7 and TLR8, two novel members, are registered in GenBank (Registration No: AF240467 and AF246971). Although full-length cDNA is also found out for TLR9, and is registered in GenBank (Registration No: AF245704), its function has not been known.

The present invention relates to DNA encoding a receptor protein specifically recognizing bacterial DNA having an unmethylated CpG sequence ("1"), the protein according to "1" wherein a receptor protein specifically recognizing bacterial DNA having an unmethylated CpG sequence is either of the following proteins (a) or (b): (a) a protein comprising the sequence of amino acids shown in Seq. ID No: 2, or (b) a protein comprising a sequence of amino acids wherein one or more of amino acids are deleted, substituted, or added in the sequence of amino acids shown in Seq. ID No: 2, and having reactivity against bacterial DNA having an unmethylated CpG sequence ("2"), the DNA according to "1" comprising the sequence of bases shown in Seq. ID No: 1 or its complementary sequence, or part or whole of the sequences ("3"), the DNA according to "1" which hybridizes with the DNA comprising a gene according to "3" under a stringent condition ("4"), the protein according to "1" wherein a receptor protein specifically recognizing bacterial DNA having an unmethylated CpG sequence is either of the following proteins (a) or (b): (a) a protein comprising the sequence of amino acids shown in Seq. ID No: 4, or (b) a protein comprising a sequence of amino acids wherein one or more of amino acid are deleted, substituted, or added in the sequence of amino acids shown in Seq. ID No: 4, and having reactivity against bacterial DNA having an unmethylated CpG sequence ("5"), the DNA according to "1" comprising the sequence of bases shown in Seq. ID No: 3 or its complementary sequence, or part or whole of the sequences ("6"), and the DNA according to "1" which hybridizes with the DNA comprising the gene according to "6" under a stringent condition ("7").

The present invention also relates to a receptor protein specifically recognizing bacterial DNA having an unmethylated CpG sequence ("8"), the protein according to "8" comprising the sequence of amino acids shown in Seq. ID No: 2 ("9"), the protein according to "8" comprising a sequence of amino acids wherein one or more of amino acids are deleted, substituted or added in the sequence of amino acids shown in Seq. ID No: 2 ("10"), the protein according to "8" comprising the sequence of amino acids shown in Seq. ID No: 4 ("11"), and the protein according to "8" comprising a sequence of amino acids wherein one or more of amino acids are deleted, substituted or added in the sequence of amino acids shown in Seq. ID No: 4 ("12").

The present invention also relates to a fusion protein comprising the protein according to any one of "8" to "12" fused with a marker protein and/or a peptide tag ("13") an antibody specifically bound to the protein according to any one of "8" to "12"( "14"), the antibody according to "14" which is a monoclonal antibody ("15"), a host cell comprising an expression system expressing the protein according to any one of "8" to "12"("16").

The present invention also relates to a non-human animal wherein a gene encoding a receptor protein specifically recognizing bacterial DNA having an unmethylated CpG sequence is excessively expressed ("17"), a non-human animal wherein a gene function encoding a receptor protein specifically recognizing bacterial DNA having an unmethylated CpG sequence is destroyed on a chromosome ("18"), the non-human animal according to "18" having no reactivity against bacterial DNA having an unmethylated CpG sequence ("19"), the non-human animal according to any one of "17" to "19" characterized in that a rodent animal is a mouse ("20").

The present invention also relates to a method of preparing a cell expressing a protein having reactivity against bacterial DNA having an unmethylated CpG sequence characterized in that the DNA according to any one of "1" to "7" is introduced into a cell wherein a gene function encoding a receptor protein specifically recognizing bacterial DNA having an unmethylated CpG sequence is destroyed on a chromosome ("21"), and a cell expressing a receptor protein specifically recognizing bacterial DNA having an unmethylated CpQ sequence obtained by the method of preparing a cell expressing a receptor protein specifically recognizing bacterial DNA having an unmethylated CpG sequence according to "21" ("22").

The present invention also relates to screening method for an agonist or an antagonist of a receptor protein specifically recognizing bacterial DNA having an unmethylated CpG sequence comprising steps of: in vitro culturing a cell expressing a receptor protein specifically recognizing bacterial DNA having an unmethylated CpG sequence in the presence of a target substance, and measuring/evaluating TLR9 activity ("23"), a screening method for an agonist or an antagonist of a receptor protein specifically recognizing bacterial DNA having an unmethylated CpG sequence comprising steps of administrating a target substance to a non-human animal wherein a gene function encoding a receptor protein specifically recognizing bacterial DNA having an unmethylated CpG sequence is destroyed on a chromosome, and measuring/evaluating TLR9 activity of macrophages or spleen cells obtained from the non-human animal ("24"), a screening method for an agonist or an antagonist of a receptor protein specifically recognizing bacterial DNA having an unmethylated CpG sequence comprising steps of: administrating a target substance to a non-human animal wherein a gene encoding a receptor protein specifically recognizing bacterial DNA having an unmethylated CpG sequence is excessively expressed, and measuring/evaluating TLR9 activity of macrophages or spleen cells obtained from the non-human animal ("25"), a screening method for an agonist or an antagonist of a protein having reactivity against bacterial DNA having the unmethylated CpG sequence according to either of "24" or "25" using a mouse as a non-human animal ("26").

The present invention also relates to an agonist or an antagonist of a receptor protein specifically recognizing bacterial DNA having an unmethylated CpG sequence obtained by the screening method for an agonist or an antagonist of a receptor protein specifically recognizing bacterial DNA having the unmethylated CpG sequence according to any one of "23" to "26"("27"), a pharmaceutical composition comprising whole or part of a receptor protein specifically recognizing bacterial DNA having an unmethylated CpG sequence as an active component ("28"), a pharmaceutical composition comprising the agonist or antagonist according to "27" as an active component ("29"), a kit used to diagnose diseases related to the deletion, substitution and/or addition in a sequence of DNA encoding a receptor protein specifically recognizing bacterial DNA having an unmethylated CpG sequence comprising the DNA according to "3", which can compare a sequence of DNA encoding a receptor protein specifically recognizing bacterial DNA having an unmethylated CpG sequence in a test body with a sequence of bases in the DNA according to "3"("30").

BRIEF DESCRIPTION OF THE DRAWINGS

FIG. 4 shows the result of comparing the sequence of amino acids from TLR9 knockout mice in the present invention and the sequence of amino acids from wild-type mice (SEQ ID NOS 6-9 disclosed respectively in order of appearance).

FIG. 5 shows the result of measurement of TNFα, IL-6 or IL-12 production induced by CpG ODN, PGN or LPS in TLR9 knockout mice in the present invention and in wild-type mice.

BEST MODE TO CARRY OUT THE PRESENT INVENTION

Figure 1:
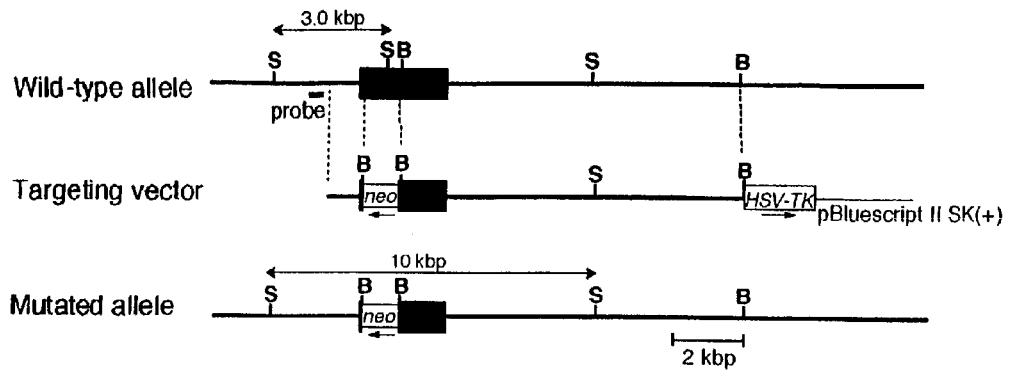
FIG. 1 shows a gene maps of TLR9 knockout mice in the present invention and wild-type mice.

As bacterial DNA comprising an unmethylated CpG sequence in the present invention, any DNA derived from bacteria such as an oligodeoxynucleotide having an unmethylated CpG motif which activates immune cells such as T-cells, B-cells and antigen-presenting cells, and induces immune response can be used such as DNA derived from bacteria including *Escherichia coli, Klebsiella pneumoniae, Pseudomonas aeruginosa, Salmonella Typhimurium, Serratia marcescens, Shigella flexneri, Vibrio cholerae, Salmonella Minnesota, Porphylomonas gingivalis, Staphylococcus aureus, Corynebacterium diphtheriae, Nocardia coeliaca, Streptococcus pneumoniae.*

As a receptor protein specifically recognizing bacterial DNA having the unmethylated CpG motif, there are no particular restrictions as long as the protein can specifically recognize bacterial DNA with an unmethylated CpG sequence, and can be exemplified by human-derived TLR9 shown in Seq. ID No. 2 in the list of sequence, a protein which comprises a sequence of amino acids wherein one or more of amino acids are deleted, substituted, or added in a sequence of amino acids shown in Seq. ID No: 2, and which specifically recognizes bacterial DNA having the unmethylated CpG sequence, or their recombinant proteins. The receptor protein specifically recognizing bacterial DNA having the unmethylated CpG sequence can be prepared by well known methods based on the information of the DNA sequence and others.

DNA encoding a receptor protein specifically recognizing bacterial DNA having an unmethylated CpG sequence of the present invention includes DNA encoding human-derived TLR9 shown in Seq. ID No: 2 in the list of sequence such as the one shown in Seq. ID No: 1, DNA comprising a sequence of amino acids wherein one or more of amino acids are deleted, substituted or added in a sequence of amino acids shown in Seq. ID No: 2, and which can specifically recognize bacterial DNA having the unmethylated CpG sequence mentioned above, or DNA hybridized with the DNA under stringent conditions and encoding a protein that can specifically recognize bacterial DNA having the unmethylated CpG sequence mentioned above. These can be prepared by well known methods based on the information of DNA sequence such as mouse RAW264.7 cDNA library or 129/SvJ mouse gene library for mouse-derived TLR9.

Further, it is possible to obtain DNA encoding a receptor protein specifically recognizing bacterial DNA having an immune-inducing unmethylated CpG sequence which has the same effect as TLR9, a receptor protein, by hybridizing mouse-derived DNA library with part or whole of a sequence of bases shown in Seq. ID No: 1 or its complementary sequence under stringent conditions to isolate the DNA hybridized with the probe. Conditions on hybridization to obtain the DNA can, for example, be hybridization at 42° C. and wash treatment at 42° C. with a buffer containing 1% ×SSC and 0.1% of SDS, and more preferably be hybridization at 65° C. and wash treatment at 65° C. with a buffer containing 0.1×SSC and 0.1% of SDS. Furthermore, beside the temperature conditions mentioned above, there are various factors effecting the stringency of hybridization, and it is possible for a person skilled in the art to realize the stringency equivalent to the stringency of hybridization illustrated above.

A fusion protein in the present invention can be the one obtained by combining a receptor protein specifically recognizing bacterial DNA having an unmethylated CpG sequence derived from mouse, human, and others with a marker protein and/or a peptide tag. A marker protein can be any marker protein previously well known, and can be exemplified by alkaline phosphatase, Fc region of an antibody, HRP, GFP and others. As a peptide tag in the present invention, it can be concretely exemplified by previously well-known peptide tags such as Myc tag, His tag, FLAG tag, GST tag. The fusion protein can be produced by a normal method, and is useful in purifying a receptor protein specifically recognizing bacterial DNA having an unmethylated CpG sequence by using affinity of Ni-NTA and His tag, detecting a receptor protein specifically recognizing bacterial DNA having an unmethylated CpG sequence, measuring of the amount of antibodies against a receptor protein specifically recognizing bacterial DNA having an unmethylated CpG sequence and as a research reagent in other relevant fields.

As an antibody specifically bound to a receptor protein specifically recognizing bacterial DNA having an unmethylated CpG sequence in the present invention, it can be concretely exemplified by immune-specific antibodies such as a monoclonal antibody, a polyclonal antibody, a chimeric antibody, a single-chain antibody, a humanizied antibody. These antibodies can be produced by a normal method by using a receptor protein specifically recognizing bacterial DNA having an unmethylated CpG sequence mentioned above as an antigen, and a monoclonal antibody is preferable in its specificity among them. The antibody specifically bound to a receptor protein specifically recognizing bacterial DNA having an unmethylated CpG sequence such as a monoclonal antibody and others is useful, for example, in diagnosing diseases caused by the mutation or deletion of TLR9 or elucidating the molecular mechanism controlling TLR9.

An antibody against a receptor protein specifically recognizing bacterial DNA having an unmethylated CpG sequence can be produced by administrating a fragment containing a receptor protein or an epitope specifically recognizing bacterial DNA having the unmethylated CpG sequence in animals (preferably, non-human), or a cell expressing the protein on the surface of its membrane by a conventional protocol, and any method can be used such as hybridoma method (Nature 256, 495-497, 1975), trioma method, human B cell hybridoma method (Immunology Today 4, 72, 1983), and EBV-hybridoma method (MONOCLONAL ANTIBODIES AND CANCER THERAPY, 77-96, Alan R. Liss, Inc., 1985), which are used for preparing monoclonal antibodies and brings an antibody produced by the cultured successive cell lines. The following explains a method of producing a monoclonal antibody specifically bound to mouse-driven TLR9, that is, an mTLR9 monoclonal antibody, with mouse-driven TLR9 as an example of a receptor protein specifically recognizing bacterial DNA having an unmethylated CpG sequence.

The mTLR9 monoclonal antibody can be produced by a normal method of culturing hybridoma producing mTLR9 monoclonal antibody in vivo or in vitro. For example, in an in vivo systems they can be obtained by culturing in the visceral cavity of rodents, preferably of mice or rats, and in an in vitro system they can be obtained by culturing in a medium for culturing animal cells. A medium used for culturing hybridoma in an in vitro system can be exemplified by cell culture media such as RPMI1640 or MEN and others comprising antibiotics such as streptomycin or penicillin.

The hybridoma producing mTLR9 monoclonal antibody can be produced by immunizing BALB/c mouse with TLR9, a receptor protein obtained from mouse and others, fusing a spleen cell from an immunized mouse and a mouse NS-1 cell (ATCC TIB-18) by a normal method, and screening them by immunofluorescence staining patterns. A method of separating/isolating the monoclonal antibody can be any one as long as it is a method usually used for purifying proteins, and liquid chromatography such as affinity chromatography and others can be a concrete example.

It is also possible to apply the method of a single-chain antibody (U.S. Pat. No. 4,946,778) to produce single-chain antibodies against receptor proteins specifically recognizing bacterial DNA having the above-mentioned unmethylated CpG sequence of the present invention. Further, it is possible to use transgenic mice or other mammals and the like to express humanized antibodies, isolate/identify the clones expressing a receptor protein specifically recognizing bacterial DNA having an unmethylated CpG sequence by using the antibodies, and purify the polypeptides by affinity chromatography. The antibodies against receptor proteins specifically recognizing bacterial DNA having an unmethylated CpG sequence are useful in elucidating the molecular mechanism of a receptor protein specifically recognizing bacterial DNA having an unmethylated CpG sequence.

It is also possible to carry out a functional analysis of a receptor protein specifically recognizing bacterial DNA having the unmethylated CpG sequence by using fusion proteins obtained by fusing proteins labeled with fluorescent substances such as FITC (fluorescein isothiocyanate) or tetramethylrhodamine isocyanate, fusion proteins labeled with radio isotopes such as $^{125}I$, $^{32}P$, $^{35}S$ or $^{3}H$, enzymes such as Alkaline phosphotase, peroxidase, β-Galacotsidase or Phycoerythrin, or fluorescent proteins such as Green Fluorescent Protein (GFP). A method of immunoassay can be exemplified by RIA, ELISA, fluorescence antibody method, plaque forming cell assay, spot method, hemagglutination reaction method, Ouchterlony Method, and others.

The present invention relates to a host cell comprising an expressing system that can express a receptor protein specifically recognizing bacterial DNA having the unmethylated CpG sequence. Introduction of a gene encoding a receptor protein specifically recognizing bacterial DNA having the unmethylated CpG sequence into a host cell can be carried out by the methods described in a number of standard laboratory manuals such as in Davis et al. (BASIC METHODS IN MOLECULAR BIOLOGY, 1986) and Sambrook et al. (MOLECULAR CLONING: A LABORATORY MANUAL, 2nd Ed., Cold Spring Harbor Laboratory Press, Cold Spring Harbor, N.Y., 1989), such as calcium phosphate transfection, DEAE-dextran-mediated transfection, transvection, microinjection, cationic lipid-mediated transfection, electroporation, transduction, scrape loading, ballistic introduction, infection and others. A host cell can be exemplified by bacterial prokaryotes such as Escherichia coli, Streptomyces, Bacillus subtitlis, Streptococcus, Staphylococcus and others, fungal cells such as yeast and Aspergillus, insect cells such as Dorsophilia S2 or Spodoptera Sf9 and others, and animal and plant cells such as L cell, CHO cell, COS cell, Hela cell, C127 cell, BALB/c3T3 cell (including mutant strains lacking dihydrofolate reductase, thymidine kinase or others), BHK 21 cell, HEK293 cell, Bowes Melanoma cell, oocytes, and others.

Further, the expression system can be any one as long as it is a system that can express a receptor protein specifically recognizing bacterial DNA having the unmethylated CpG sequence in a host cell, and can be exemplified by expression systems derived from chromosome, episome and virus, such as vectors derived from bacterial plasmid, yeast plasmid, papovavirus such as SV40, vaccinia virus, adeno virus, fowl poxvirus, pseudorabies virus, or vectors derived from retrovirus, vectors derived from bacteriophage or transposon or their combinations, which can be exemplified by plasmids such as cosmid and phagemid, which are derived from genetic factors of plasmids and bacteriophage. These expressing systems may comprise a control sequence that not only causes expression but also regulates expression.

A receptor protein specifically recognizing a host cell comprising the expressing system or a cell membrane of the cell, bacterial DNA comprising an unmethylated CpG sequence obtained by culturing, and the cell can be used for the screening methods of the present invention as mentioned below. For example, a method described in F. Pietri-Rouxel et al. (Eur. J. Biochem., 247, 1174-1179, 1997) can be used as a method for obtaining cell membrane, and well known methods including ammonium sulfate or ethanol precipitation, acid extraction, anion- or cation-exchange chromatography, phosphocellulose chromatography, hydrophobic interaction chromatography, affinity chromatography, hydroxyapatite chromatography and lectin chromatography, preferably high-performance liquid chromatography can be used to collect a receptor protein specifically recognizing bacterial DNA having the unmethylated CpG sequence from the cell culture and to purify it. Specifically, it is possible to obtain a receptor protein specifically recognizing the bacterial DNA having an unmethylated CpG sequence by using a column to which a receptor protein antibody specifically recognizing bacterial DNA having the anti-unmethylated CpG sequence of anti-TLR9 monoclonal antibodies and others is bound, or in case an ordinary peptide tag is bound to a receptor protein such as TLR9 etc. specifically recognizing a column to which a substance having an affinity with a peptide tag is bound for affinity chromatography.

A non-human animal excessively expressing a gene encoding a receptor protein specifically recognizing bacterial DNA having the unmethylated CpG sequence mentioned above in the present invention can be a non-human animal producing a large amount of receptor proteins specifically recognizing bacterial DNA having an unmethylated CpG sequence compared with wild-type non-human animals. Further, a non-human animal whose gene function encoding a receptor protein specifically recognizing bacterial DNA having an unmethylated CpG sequence is deleted on the chromosome is a non-human animal wherein part or whole of genes encoding receptor proteins specifically recognizing bacterial DNA having an unmethylated CpG sequence on the a chromosome are inactivated by genetic mutations such as damaged, deleted, substituted, and others, and which lost a function of expressing a receptor protein specifically recognizing bacterial DNA having an unmethylated CpG sequence. Although the non-human animal used in the present invention can be exemplified by a non-human animal including rodents such as rabbits, mice, rats and others, it is not restricted to the animals.

Further, refractory against bacterial DNA having an unmethylated CpG sequence in the present invention means that the reactivity against stimuli by bacterial DNA shown by an organism, or a cell, a tissue or an organ constituting the organism is declined or almost totally lost. Therefore, a non-human animal with refractory against bacterial DNA having an unmethylated CpG sequence in the present invention is a non-human animal such as mice, rats, or rabbits, wherein the an organism's reactivity against bacterial DNA, or a cell, a tissue or an organ constituting the organism is declined or almost totally lost. Further, stimuli by bacterial DNA can be exemplified by an in vivo stimulus caused by administrating bacterial DNA to an organism, or an in vitro stimulus caused by contacting cells separated from an organism with bacterial DNA. Concretely, a non-human animal such as TLR9 knockout mice wherein TLR9 gene functions are destroyed on the chromosome can be an example.

A homozygote non-human animals born following Mendel's Law includes mice deficient of or excessively expressing receptor proteins specifically recognizing bacterial DNA having an unmethylated CpG sequence and their wild-type littermates, and it is preferable to use wild-type non-human animals, that is, the same kind of animal as a non-human animal wherein gene functions encoding a receptor protein specifically recognizing bacterial DNA having an unmethylated CpG sequence are destroyed or are excessive, more preferably their littermate animals, for example, during the screening of the present invention described below because accurate comparative experiments can be carried out at the level of individuals by using the homozygote non-human animals with its receptor proteins destroyed or the one with receptor proteins expressing excessively or the wild-type non-human animals born from the same mother at the same time. In the following, a method of producing non-human animals wherein gene functions encoding a receptor protein specifically recognizing bacterial DNA having the unmethylated CpG sequence are destroyed or excessively expressed on the chromosome is explained using knockout mice or transgenic mice whose receptor proteins specifically recognizing bacterial DNA having an unmethylated CpG sequence as an example.

For example, as for a mouse wherein gene functions encoding receptor proteins specifically recognizing bacterial DNA having an unmethylated CpG sequence are destroyed on a chromosome such as TLR9, that is, a knockout mouse lacking receptor proteins specifically recognizing bacterial DNA having an unmethylated CpG sequence, gene fragments obtained from mouse gene library by a method of PCR or the like are used to screen genes encoding receptor proteins specifically recognizing bacterial DNA having the unmethylated CpG sequence, subclone a gene encoding a receptor protein specifically recognizing bacterial DNA having the screened unmethylated CpG sequence with viral vectors and others, and specified by DNA sequencing. Whole or part of the gene in the clone encoding a receptor protein specifically recognizing bacterial DNA having an unmethylated CpG sequence is substituted with pMC1 neo gene cassette and others, and a targeting vector is produced by introducing diphtheria toxin A fragments (DT-A) genes or herpes simplex virus thymidine kinase (HSV-tk) genes and others on 3'-end side.

The produced targeting vector is linearized, introduced into ES cells by electroporation method and others, homologous recombination is performed, and ES cells which has caused homologous recombination by antibiotics such as G418 or gancyclovir (GANC) and others are selected from the homologous recombinants. It is preferable to confirm by Southern blot technique that the selected ES cells are targeted recombinants. The clones of the confirmed ES cells are introduced to mouse blastocysts by microinjection, and the blastcysts are returned to recipient mice, and chimera mice were produced. The chimera mouse was intercrossed with a wild-type mouse to produce a heterozygote mouse, and the heterozygote mice are intercrossed to produce a knockout mouse lacking a receptor protein specifically recognizing bacterial DNA having an unmethylated CpG sequence in the present invention. Further, a method of confirming whether knockout mice lacking a receptor protein specifically recognizing bacterial DNA having an unmethylated CpG sequence is obtained, for example, may be examined by Northern blot technique, which isolates RNA from the mouse obtained by the method mentioned above, or the expression in the mice may be examined by Western blot technique.

The fact that the produced TLR9 knockout mouse is refractory against bacterial DNA having an unmethylated CpG sequence can be confirmed by measuring the levels of the production of TNF-α, IL-6, IL-12, IFN-γ and others in the cells whose CpG ODN was contacted in vivo or in vitro with immune cells such as macrophages, mononuclear cells, dendritic cells from TLR9 knockout mice, the proliferation of response of spleen B cells, the expression of antibodies such as CD40, CD80, CD86, MHC class II on the surface of spleen B cells, and the activation of molecules on the signal transduction pathway of NF-κB, JNK, IRAK and others. The knockout mice lacking TLR9 in the present invention can be used to elucidate functional mechanisms of bacterial DNA and others having an unmethylated CpG sequence and to developing vaccine against bacterial infections.

Transgenic mice overexpressing receptor protein specifically recognizing bacterial DNA having an unmethylated CpG sequence can be generated by constructing introduced genes by fusing chicken β actin, mouse neurofilament, promotors such as SV40, and rabbit β-globin, polyA such as SV40 or intron with cDNA encoding receptor proteins specifically recognizing bacterial DNA having an unmethylated CpG sequence such as TLR9, microinjecting the introduced genes to pronucleus of mouse fertilized eggs, transplanting the obtained cells to an oviduct of recipient mice after culturing them, then breeding the transplanted animals, and selecting child mice having the cDNA from born child mice. Further, selection of the child mice having cDNA can be performed by dot hybridization wherein crude cDNA was extracted from mouse tails and others, and genes encoding receptor proteins specifically recognizing bacterial DNA having an introduced unmethylated CpG sequence is used as a probe, or PCR method using specific primers and others.

Further, the use of whole or part of DNA encoding receptor proteins specifically recognizing bacterial DNA having an unmethylated CpG sequence in the present invention enables us to prepare cells effective for genetic treatments for diseases caused by the deletion or abnormality of receptor proteins specifically recognizing bacterial DNA having an unmethylated CpG sequence. Methods of preparing the cells in the present invention can be exemplified by a method wherein part or whole of the DNA in the present invention is introduced into cells lacking gene functions encoding receptor proteins specifically recognizing bacterial DNA having an unmethylated CpG sequence on the chromosome by transfection and others, and thus obtaining a cell expressing receptor proteins specifically recognizing bacterial DNA having the unmethylated CpG sequence. It is preferable to use a cell in which the DNA and others is integrated onto the chromosome and shows TLR9 activity in a stable manner, particularly as a cell expressing receptor proteins specifically recognizing bacterial DNA having the unmethylated CpG sequence.

Furthermore, the use of DNA encoding receptor proteins specifically recognizing bacterial DNA having the unmethylated CpG sequence, antibodies against receptor proteins specifically recognizing bacterial DNA having a fused unmethylated CpG sequence comprising a receptor protein specifically recognizing bacterial DNA having an unmethylated CpG sequence bound to a marker protein and/or a peptide tag, a host cell comprising an expression system which can express a receptor protein specifically recognizing bacterial DNA having an unmethylated CpG sequence, non-human animals excessively expressing genes encoding receptor proteins specifically recognizing bacterial DNA having an unmethylated CpG sequence, non-human animals lacking gene functions encoding receptor proteins specifically recognizing bacterial DNA having an unmethylated CpG sequence on a chromosome, cells expressing receptor proteins specifically recognizing bacterial DNA having an unmethylated CpG sequence enables us to screen agonists or antagonists of the receptor proteins specifically recognizing bacterial DNA having an unmethylated CpG sequence in the present invention, or suppressing or promoting substances reactive to bacterial DNA having an unmethylated CpG sequence. What is obtained by the screening may be suppressing or promoting substances against bacterial infected diseases, suppressing agents, preventing agents or remedies against allergic diseases or cancers, agents suppressing or promoting side effects in genetic therapy or the like, or substances useful for diagnosing/treating diseases or the like caused by the deletion or abnormality of TLR9 activity.

Although the TLR activities can concretely be exemplified by a function of reacting specifically to bacterial DNA having an unmethylated CpG sequence and transmitting signals into cells, and a signal transduction function is a function of producing cytokines such as TNF-α, IL-6, IL-12, IFN-γ or the like, a function of producing nitrous acid ion, a function of proliferating cells, a function of expressing antibodies such as CD40, CD80, CD86, MHC class II and others on the surface of cells, and a function of activating molecules in signal transduction pathway of TLR9 such as NF-κB, JNK, IRAK and others, it is not limited to these functions.

A screening method of agonists or antagonists of receptor proteins specifically recognizing bacterial DNA having an unmethylated CpG sequence in the present invention can concretely be exemplified by a method of performing in vitro culture of immune cells such as macrophages, spleen cells or dendritic cells, cells expressing a receptor protein specifically recognizing bacterial DNA having an unmethylated CpG sequence, cells expressing a protein having reactivity against bacterial DNA having an unmethylated CpG sequence in a cell expressing a receptor protein specifically recognizing bacterial DNA having an unmethylated CpG sequence under the presence of target substance, and measuring/evaluating TLR9 activities, or a method of administrating target substance to wild-type non-human animals, non-human animals lacking a gene function of encoding receptor proteins specifically recognizing bacterial DNA an unmethylated CpG sequence, or non-human animals excessively expressing genes encoding receptor proteins specifically recognizing bacterial DNA having an unmethylated CpG sequence, and measuring/evaluating TLR 9 activities of immune cells such as macrophages, spleen cells or dendritic cells derived from these non-human animals.

Further, in evaluating and measuring the levels of macrophage activities or spleen cell activities, it is preferable to evaluate and compare them with the measurement values obtained from wild-type non-human animals, especially wild-type non-human animals born from the same parent to remove variances arising from individual differences. The same also applies to screening of suppressing or promoting substances reactive to bacterial DNA having an unmethylated CpG sequence shown below.

Screening methods for suppressing or promoting substances reactive to bacterial DNA having an unmethylated CpG sequence can concretely be exemplified by a method comprising the steps of carrying out in vitro incubation of proteins or cell membranes expressing the proteins having a reactivity against bacterial DNA having an unmethylated CpG sequence under the presence of target substances and bacterial DNA having an unmethylated CpG sequence, measuring/evaluating the reactivity of the protein, or a method comprising the steps of first making macrophages or spleen cells obtained from non-human animals whose gene functions encoding proteins having reactivity against bacterial DNA having an unmethylated CpG sequence are destroyed on a chromosome contact in vitro with target substances, then culturing the macrophages or spleen cells in the presence of bacterial DNA having an unmethylated CpG sequence, and measuring/evaluating the levels of macrophage activities shown by the macrophages or the levels of spleen cell activities shown by the spleen cells, a method comprising the steps of making macrophages or spleen cells obtained from non-human animals whose gene functions encoding proteins having reactivity against bacterial DNA having an unmethylated CpG sequence contact in vitro with bacterial DNA having an unmethylated CpG sequence, then culturing the macrophages or spleen cells in the presence of target substances, and measuring/evaluating the levels of macrophage activities shown by the macrophages or the levels of spleen cell activities shown by the spleen cells, and a method of comprising the steps of first administrating target substances to non-human animals whose gene functions encoding proteins having reactivity against bacterial DNA having an unmethylated CpG sequence on a chromosome first, then culturing the macrophages or spleen cells obtained from the non-human animals in the presence of bacterial DNA having an unmethylated CpG sequence, and measuring/evaluating the levels of macrophage activities shown by the macrophages or the levels of spleen cell activities shown by the spleen cells, a method comprising the steps of first administrating target substances to non-human animals whose gene functions encoding proteins having reactivity against bacterial DNA having an unmethylated CpG sequence is destroyed on a chromosome, then infecting the non-human animals by bacteria, and measuring/evaluating the levels of macrophage activities shown by macrophages or the levels of spleen cell activities shown by the spleen cells obtained from non-human animals, a method of the steps of first administrating target substance to non-human animals whose gene functions encoding proteins having reactivity against bacterial DNA having an unmethylated CpG sequence on a chromosome, and measuring/evaluating the levels of macrophage activities shown by macrophages or the levels of spleen cell activities shown by spleen cells obtained from the non-human animals, a method comprising the steps of first infecting with bacteria non-human animals whose gene functions encoding proteins having reactivity against bacterial DNA having an unmethylated CpG sequence are destroyed on a chromosome, then culturing macrophages or spleen cells obtained from the non-human animals in the presence of target substances, and measuring/evaluating the levels of macrophage activities shown by macrophages or the levels of spleen cell activities shown by spleen cells obtained from the non-human animals, a method comprising the steps of administrating target substances to non-human animals whose gene functions are encoding proteins having reactivity against bacterial DNA having an unmethylated CpG sequence are destroyed, infecting the non-human animals by bacteria, and measuring/evaluating the levels of macrophage activities or spleen cell activities in the non-human animals, and a method comprising the steps of infecting non-human animals whose gene functions encoding proteins having reactivity against bacterial DNA having an unmethylated CpG sequence are destroyed on a chromosome first, then administrating the target substances to the non-human animals, and measuring/evaluating the levels of macrophage activities or spleen cell activities in the non-human animals. Although as bacterial DNA having an unmethylated CpG sequence used in the screening methods, it is preferable to use CpG ODN (TCC-ATG-ACG-TTC-CTG-ATG-CT: Seq. ID No: 5), it is not limited to this.

The present invention also relates to a kit used to diagnose diseases relating to the activity or expression of receptor proteins specifically recognizing bacterial DNA having an unmethylated CpG sequence by comparing a sequence of DNA encoding receptor proteins specifically recognizing bacterial DNA having an unmethylated CpG sequence in a test body with a sequence of DNA encoding receptor proteins specifically recognizing bacterial DNA having an unmethylated CpG sequence in the present invention. The detection of mutated DNA encoding receptor proteins specifically recognizing bacterial DNA having an unmethylated CpG sequence can be carried out by detecting genetically mutated individuals at the level of DNA, and is effective for diagnosing diseases caused by hypotypic expression, hypertypic expression or mutated expression of receptor proteins specifically recognizing bacterial DNA having an unmethylated CpG sequence. Although a test body used in the detection can concretely be exemplified by genomic DNA of cells from subjects obtainable by biopsy from blood, urine, saliva, tissue and others, RNA, or cDNA, it is not limited to these. In using the test body, it is possible to use the ones amplified by PCR and others. The deficiency or insertional mutation in sequences of bases can be detected by the changes of amplified products in size compared with normal genes, and point mutation can be identified by hybridizing the amplified DNA with the gene encoding receptor proteins specifically recognizing bacterial DNA having labeled unmethylated CpG sequence. It is possible to diagnose or conclude diseases relevant to activity or expression of receptor proteins specifically recognizing bacterial DNA having an unmethylated CpG sequence by detecting mutation of a gene encoding receptor proteins specifically recognizing bacterial DNA having an unmethylated CpG sequence.

The present invention also relates to a probe diagnosing a disease related to activities or expressions of a receptor protein specifically recognizing bacterial DNA having an unmethylated CpG sequence comprising whole or part of antisense chain of DNA or RNA encoding a receptor protein specifically recognizing bacterial DNA having an unmethylated CpG sequence, and a kit used to diagnose diseases relating to activities or expressions of a receptor protein specifically recognizing bacterial DNA having an unmethylated CpG sequence comprising an antibody specifically bound to a receptor protein specifically recognizing bacterial DNA having an unmethylated CpG sequence of the probe and/or in the present invention. A probe used for the diagnosis is whole or part of an antisense chain of DNA (cDNA) or RNA (cRNA) encoding a receptor protein specifically recognizing bacterial DNA having an unmethylated CpG sequence, and there is no limitations on the probe as long as it is long enough (at least 20 bases or more) to establish as a probe. In order to make an antibody specifically bound to a receptor protein specifically recognizing bacterial DNA having an unmethylated CpG sequence of the probe and/or in the present invention an active component of a medicine diagnosing diseases such as bacterial infection and others, it is preferable to dissolve it into appropriate buffers or sterilized water in which a probe is not decomposed. Further, it is possible to use the clinical test pharmaceuticals to diagnose a patient's symptoms such as bacterial infection diseases and others in the ways such as immunofluorescence (Dev. Biol. 170, 207-222, 1995, J. Neurobiol. 29, 1-17, 1996), In situ hybridization (J. Neurobiol. 29, 1-17, 1996), or in situ PCR or others.

A pharmaceutical composition of the present invention can be any one as long as it comprises whole or part of the receptor protein specifically recognizing bacterial DNA having an unmethylated CpG sequence of TLR9 or others, or comprises an agonist or an antagonist of the receptor protein. Concretely, vaccines against bacterial infectious diseases, vaccines against cancers, treating medicine for patients having allergies such as bronchial asthma, reversal agents, suppressing agents, inhibiting agents and others for side effects by the existence of a CpG motif inhibiting genetic treatments or treatments using antisenseoligonucleotides can be exemplified.

As mentioned above, a kit testing diagnoses relevant to the deletion, substitution and/or addition of DNA sequence encoding a receptor proteins specifically recognizing bacterial DNA having an unmethylated CpG sequence of the present invention can be any one as long as it comprises DNA encoding TLR9, and comparing a sequence of bases of DNA encoding the TLR9 with a sequence of bases of DNA encoding a receptor protein specifically recognizing bacterial DNA having an unmethylated CpG sequence in a tested body enables us to diagnose diseases related to deletion, substitution and/or addition of DNA sequence encoding a receptor protein specifically recognizing bacterial DNA having an unmethylated CpG sequence such as cancer, allergy, infectious diseases and others.

In the following, the present invention will further be explained with concrete examples. However, the technical scope of the present invention is not limited in any way by the following examples.

EXAMPLE 1

Cloning of TLR9

As a result of a GenBank search using the information of DNA sequence of human TLR4, a mouse EST having a significant homology (Registration No. AA273731; mouse) was found. Using PCR amplified mouse EST as a probe, mouse RAW 264.7 cDNA library was screened and a full length cDNA clone shown in Seq. ID No. 3 comprising the complete TLR9 open reading frame was isolated. Performing a GenBank search based on the information of DNA sequence of the mouse TLR9, a human genomic sequence having a high level of homology was found. Based on the human genomic sequence, cDNA ends were amplified to isolate cDNA of the full length human TLR9 having a sequence of bases in Seq. ID No. 1 from U937 cells (J. Immunol. 163, 5039-5048, 1999).

EXAMPLE 2

Production of TLR Knockout Mice

The TLR9 genomic DNA was isolated from 129/SvJ mouse genomic library (Stratagene), subcloned in pBluescript II SK(+) vectors (Stratagene), and characterized by restriction enzyme mapping and DNA sequencing analysis. The targeting vector was constructed by replacing a 1.0 kb fragment encoding part of LRR (leucine-rich repeat) region with a neomycin-resistance gene cassette (pMC1-neo; Stratagene), and a herpes simplex virus thymidine kinase (HSV-TK) was inserted for negative selection (FIG. 1). The targeting vector was linearlized, and was electroporated into embryonic stem cells (ES cells) of E14-1, then 292 pieces of clones showing G418 and gancyclovir resistance were selected, and 14 pieces of clones were screened by PCR and Southern blotting.

Figure 2:
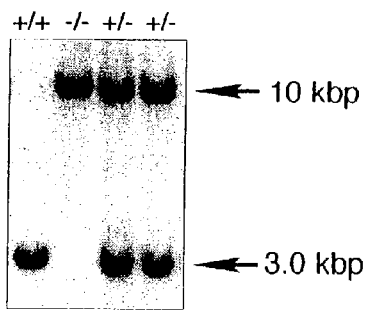
FIG. 2 shows the result of Southern blot analysis of TLR9 knockout mice in the present invention.

Chimeric mice were produced by microinjecting 3 pieces of targeted ES clones comprising mutated TLR9 allele into C57BL/6 mouse blastocysts. The male chimeric mice were intercrossed with C57BL/6 female mice to produce a heterozygote F1 mouse, and a homozygote mice (TLR9 knockout mouse: TLR9$^{-/-}$) was obtained by intercrossing heterozygote F1 mouse (FIG. 2). To confirm that the obtained mouse was homozygote, various genomic DNA extracted from a mouse tail was digested by ScaI to perform Southern blotting using the probe shown in FIG. 1. The TLR9 knockout mice (TLR9$^{-/-}$) of the present invention were produced following Mendel's law, and had not shown remarkable abnormality for 12 weeks.

Figure 3:
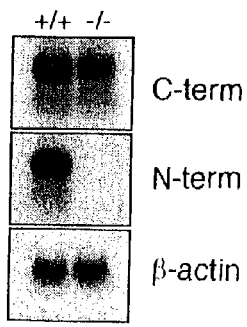
FIG. 3 shows the result of Northern blot analysis of spleen cells from TLR9 knockout mice in the present invention.

To confirm that the inactivation of TLR9 arises by mutation, total RNA (10 µg) extracted from spleen cells from wild-type mice (+/+) and TLR9 knockout mice (−/−) was electrophoresed, and transferred to nylon membranes, Northern blotting was performed with the use of cDNA specific to TLR9 c-terminal fragments or N-terminal fragments labeled with [$^{32}$P], or β-actin (FIG. 3). The result shows that N-terminal fragments of TLR9 mRNA were not detected from the spleen cells of TLR9 knockout mice. Further, with a C-terminal fragment as a probe, almost the same size of Tlr9 transcripts derived from mutated mice as the ones from wild-type mice were detected. However, the amount of the production was small. Then, RT-PCR was performed using mRNA of spleen cells obtained from mutated mice to sequence the obtained products. The result shows that the Tlr9 gene transcript comprises neo gene, and stop codons appear in a N-terminal domain of TLR9 by inserting the neo, and functional TLR9 proteins does not appear in mutated mice (FIG. 4). Further, as a result of examining lymph cells from TLR9 by flowcytometry knockout mice, no abnormal compositions were found.

EXAMPLE 3

Preparation of Peritoneal Macrophages 2 ml of 4% thioglycolic acid medium (DIFCO) was injected to each peritoneum of wild-type mice and TLR9 knockout mice (TLR9$^{-/-}$), peritoneal exudation cells were isolated from peritonea from each mouse after 3 days, the cells were cultured in RPMI1640 medium to which 10% of fetal bovine serum (GIBCO) was added at 37° C. for 2 hours, and remove the unattached cells by washing with ice-chilled Hank's buffered salt solution (HBSS; GIBCO), and the attached cells were used as peritoneal macrophages in the following experiments.

EXPERIMENT 4 Response to Bacterial DNA Having an Unmethylated CpG Sequence in TLR9 Knockout Mice It has recently been shown that the response of CpG ODN (oligodeoxynucleotide) is dependent on MyD88, an adopter protein in a signaling transduction pathway mediating TLR. Although the MyD88 knockout mice do not show response to CpG ODN, TLR2 knockout mice or TLR4 knockout mice show normal response to it. This shows that CpG ODN recognizes TLRs other than TLR2 and TLR4, and then the response of a TLR9 knockout mouse against CpG ODN was examined. First, the amount of producing inflammatory cytokines in peritoneal macrophages were measured in the following way.

The macrophages prepared in Example 3 are co-cultured with various concentrations of CpG ODN shown in FIG. 5 (0.1 or 1.0 µM; TIB MOLBIOL; TCC-ATG-ACG-TTC-CTG-ATG-CT) (SEQ ID NO: 5), PGN (10 µg/ml; Sigma and Fluka; derived from *Staphylococcus aureus*), LPS (1.0 µg/ml; Sigma; derived from Salmonella minnesota Re-595) in the presence or absence of INFγ (30 unit/ml). The concentrations of TNFα, IL-6 and IL-12 p40 in the supernatants after culturing were measured by ELISA, and the results are shown in FIG. 5. The results show that the macrophages from wild-type mice (Wild-type) produce TNFα, IL-6 and IL-12 in response to CpG ODN, and further stimulation by IFNγ and CpG ODN increases the amount of producing TNFα, IL-6 and IL-12. However, the macrophages derived from TLR9 knockout mice (TLR9$^{-/-}$) did not produce a detectable level of inflammatory cytokines in response to CpG ODN even in the presence of IFNγ. Further, it was found that the macrophages derived from wild-type mice and TLR9 knockout mice produce almost the same level of TNFα, IL-6 and IL-12 in response to LPS or PGN (FIG. 5). Each experimental result shows the average level of n=3. N.D. in the figures means not detected.

Figure 6:
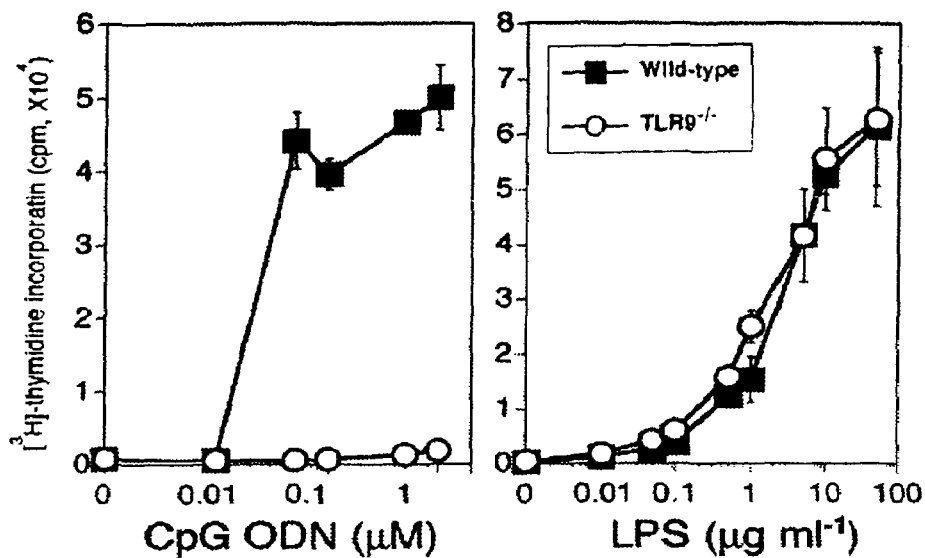
FIG. 6 shows the result of cellular proliferation response induced by CpG ODN or LPS in TLR9 knockout mice in the present invention or in wild-type mice.

Response of spleen cells from wild-type mice (Wild-type) and TLR9 knockout mice (TLR9$^{-/-}$) against CpG ODN or LPS was also examined. The spleen cells from each mouse (1×10$^5$) were isolated to culture in 96 well plates by CpG DNA or LPS of various concentrations shown in FIG. 6, and the spleen cells were stimulated. 40 hours later from culturing, 1µ Ci of [$^3$H]-timidine (Dupont) was added, and then further cultured for 8 hours. The amount of uptaking [$^3$H]-timidine was measured by β scintillation counter (Packard) (FIG. 6). The results that although the spleen cells from wild-type mice promote cell proliferating reactions depending on the amount of administrating CpG ODN or LPS, the spleen cells from TLR9 knockout mice did not show any cell proliferating reaction by CpG ODN even with the stimulus of any concentration of CpG ODN. Further, the amount of expressing Major Histocompatibility Complex (MHC) class II on the surface of B cells derived from wild-type mice in response to CpG ODN was increased. However, such increase of the amount of expressing MHC class II induced by CpG ODN in B cells derived from TLR9 knockout mice was not observed. These facts show that the macrophages or B cells from TLR9 knockout mice specifically lack the response against CpG ODN.

Figure 7:
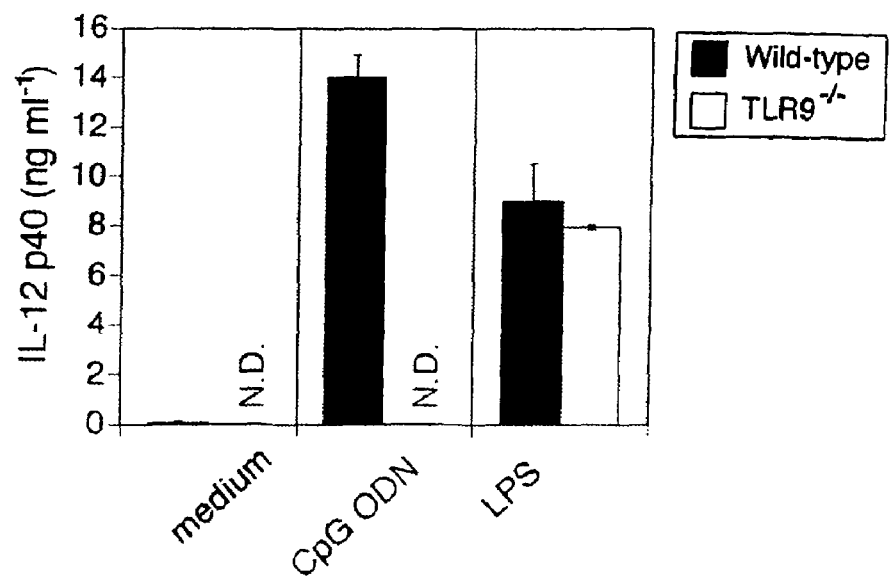
FIG. 7 shows the result of measurement of IL-12 production induced by CpG ODN or LPS in TLR9 knockout mice in the present invention or in wild-type mice.

Next, it is well known that DNA derived from bacteria comprising CpG ODN potentially stimulates dendritic cells, and supports the development of Th1 cell (EMBO J. 18, 6973-6982, 1999, J. Immunol. 161, 3042-3049, 1998, Proc. Natl. Acad. Sci. USA 96, 9305-9310, 1999). Then, the production of CpG ODN-inducing cytokines and the upregulation of the surface molecule of dendritic cells derived from bone marrow were examined. The bone marrow cells from wild-type mice (Wild-type) or TLR9 knockout mice (TLR9$^{-/-}$) were cultured with 10 ng/ml mouse granulocyte macrophage-colony stimulating factor (Peprotech) in RPMI1640 medium supplemented with 10% fetal bovine serum (J. Exp. Med. 176, 1693-1702, 1992), at day 6 of the culture, immature dendritic cells were harvested and cultured in the presence or absence of 0.1 µM CpG ODN or 0.1 µg/ml LPS in RPMI1640 medium supplemented with 10% fetal bovine serum for 2 days. After the culture, the concentration of IL-12 p40 in the supernatants was measured by ELISA (FIG. 7). The result shows that the dendritic cells derived from wild-type mice produced IL-12 in response to CpG ODN while the dendritic cells derived from TLR9 knockout mice did not induce the production of IL-12 in response to CpG ODN.

Figure 8:
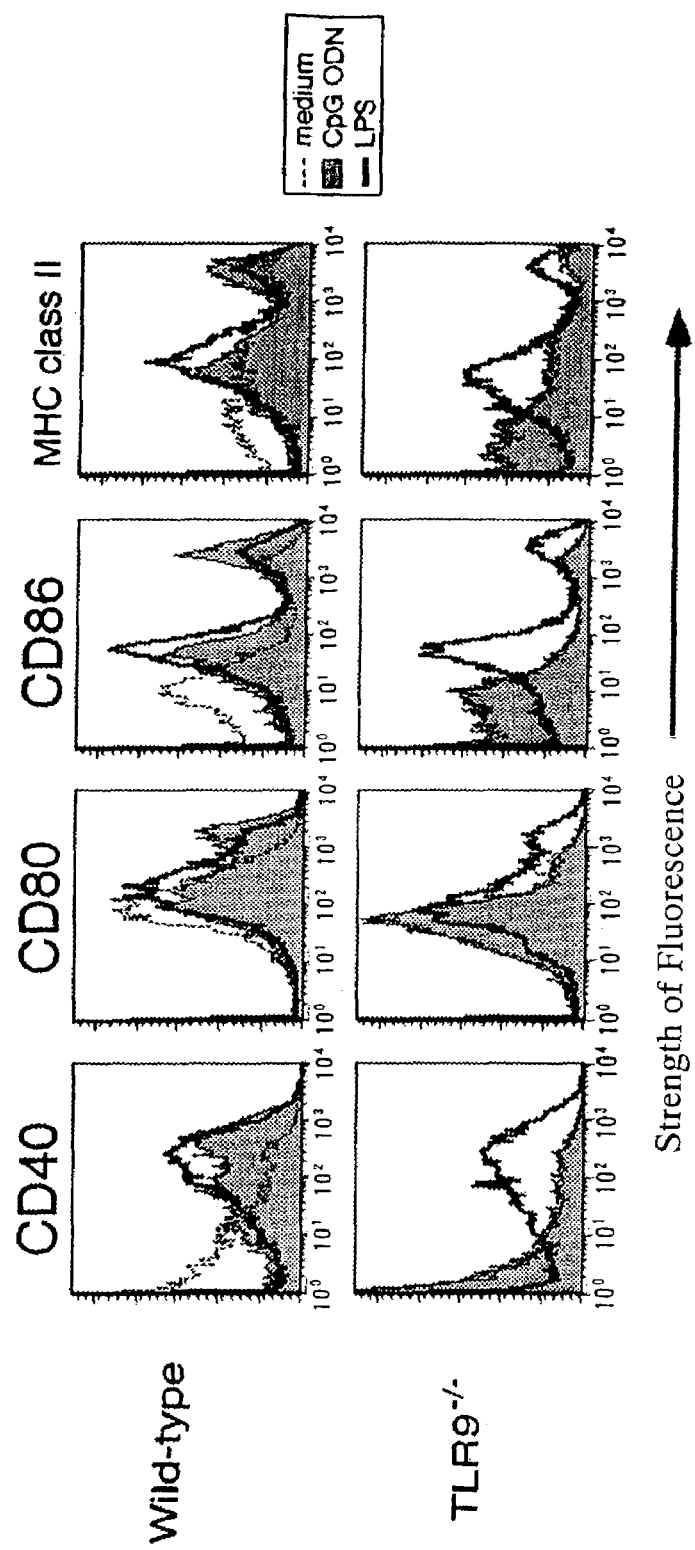
FIG. 8 shows the result of expression of CD40, CD80, CD86, and MHC class II induced by CpG ODN or LPS in TLR9 knockout mice in the present invention and in wild-type mice.

After culturing in RPMI supplemented with 10% fetal bovine serum was cultured which contains 10 ng/ml mouse granulocyte macrophage-colony stimulating factor (Peprotech), the dendritic cells harvested at day 6 were stained with biotinylated antibodies against CD40, CD80, CD86 or MHC class II, developed with streptovidine labeled with phycoerythrin (PE; PharMingen). The cells were examined by using a FACSCalibur with CELLQuest software (Becton Dickinson) (FIG. 8). The result shows that stimulation by CpG ODN promotes the expression of CD40, CD80, CD86 and MHC class II on the surface of dendritic cells derived from wild-type mouse while it does not promote the expression of these molecules on the surface of dendritic cells derived from TLR9 knockout mouse by the stimulation of CpG ODN (FIG. 8). The dendritic cells from wild-type mice and from TLR knockout mouse show similar responses in response to LPS. This result shows that TLR9 is a receptor essential for cell response to CpG ODN.

EXAMPLE 5

Figure 9:
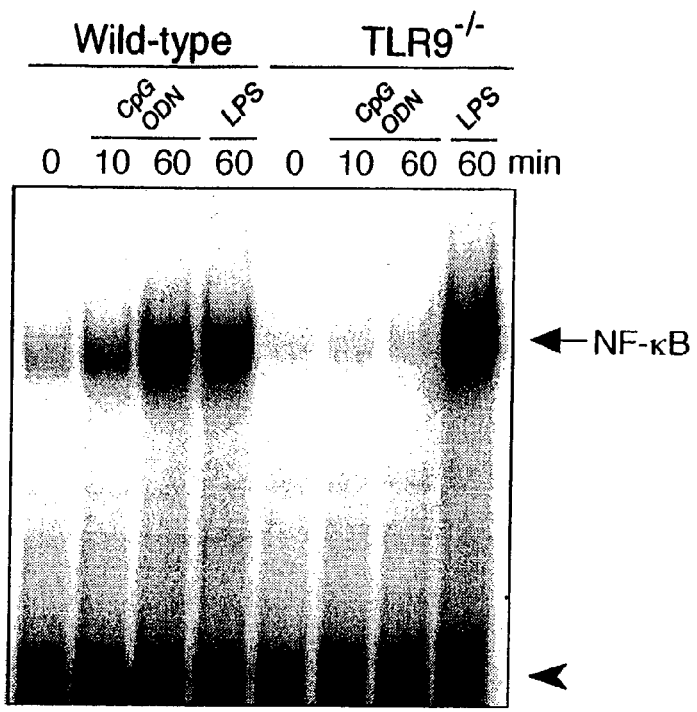
FIG. 9 shows the result of activation of NF-κB induced by CpG ODN or LPS in TLR9 knockout mice in the present invention or in wild-type mice.

Activation of NF-κB, JNK and IRAK in Response to CpG ODN of Macrophages Derived from TLR9 Knockout Mice It is known that signaling via TLRs activates IRAK, a serine-threonine kinase mediated by MyD88, an adaptor molecule, and subsequently activates MAP kinase and NF-κB (Immunity 11, 115-122, 1999). Whether CpG ODN activates the intracellular signaling or not was examined. The peritoneal macrophages ($1 \times 10^6$ cells) from wild-type and TLR9$^{-/-}$ mice in Example 3 were stimulated by 1.0 μM of CpG ODN or 1.0 μg/ml of LPS from Salmonella Minnesota Re-595 for the periods indicated in FIG. 9, nucleoproteins were extracted from the macrophages obtained from each mouse to be incubated together with a specific probe comprising NF-κB DNA-binding sites, electrophoresed, and then visualized by autoradiography (FIG. 9).

The result shows that when stimulated by CpG ODN, the macrophages derived from wild-type mice increased NF-κB DNA-binding activity while the macrophages derived from TLR9 knockout mice did not increase NF-κB DNA-binding activity. When stimulated by LPS, the macrophages derived from TLR9 knockout mice and the macrophages derived from the wild-type mice show similar NF-κB activities.

The result shows that the macrophages derived from a TLR9 knockout mouse specifically lack NF-κB activity by the induction of CpG ODN. The arrows in the figures indicate the sites of the compounds of NF-κB and specific probes, and the arrowheads indicate the sites of specific probes only.

Figure 10:
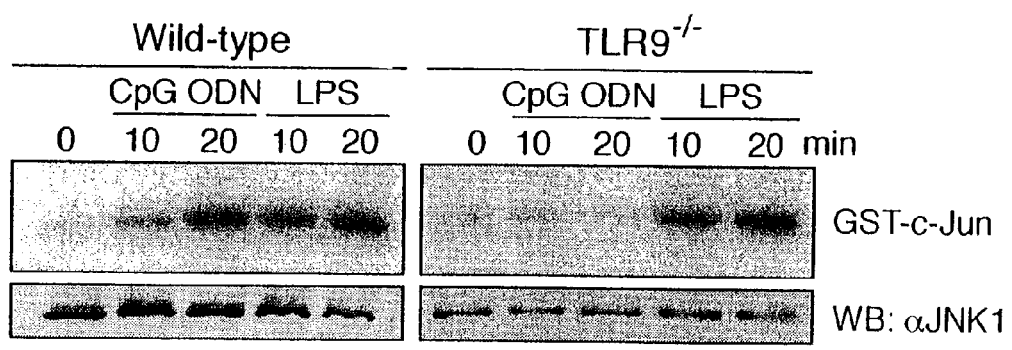
FIG. 10 shows the result of activation of JNK induced by CpG ODN or LPS in TLR9 knockout mice in the present invention or in wild-type mice.
Figure 11:
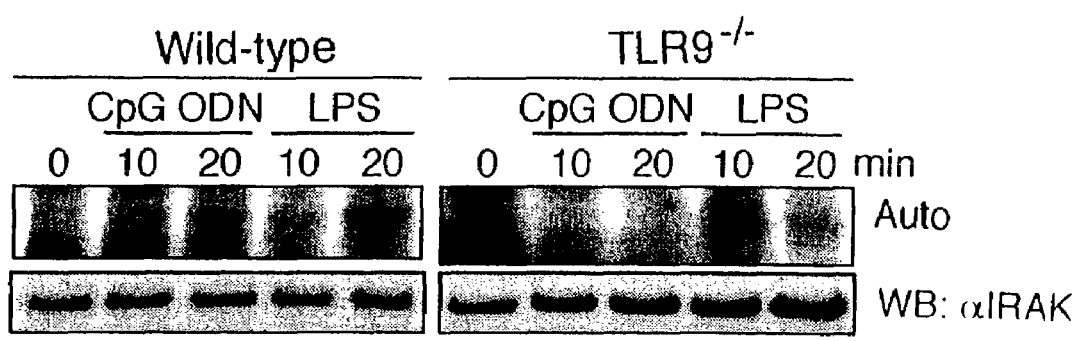
FIG. 11 shows the result of activation of IRAK induced by CpG ODN or LPS in TLR9 knockout mice in the present invention or in wild-type mice.

As shown above, the macrophages from wild-type mice and TLR9 knockout mice stimulated by CpG ODN or LPS for the periods indicated in FIG. 10 and FIG. 11 were dissolved into a solvent buffer (a buffer comprising 1.0% Triton X-100, 137 mM of NaCl, 20 mM of Tris-HCl, 5 mM of EDTA, 10% glycerol, 1 mM of PMSF, 20 μg/ml of aprotinin, 20 μg/ml of leupeptin, 1 mM of $Na_3VO_4$ and 10 mM of β-glycerophosphate at the final concentrations; pH8.0), the cell lysates were immunoprecipitated with anti-JNK antibody (Santa Cruz) or anti-IRAK antibody (Hayashibara Seikagaku Kenkyujo Kabushiki Kaisha). As described in a reference (Immunity 11, 115-122, 1999), the JNK activity and IRAK activity were measured by in vitro kinase assay using GST-c-Jun fusion protein (GST-c-Jun) as a substrate (top figures of FIG. 10 and FIG. 11; GST-c-Jun, Auto).

The cell lysates were separated by SDS-polyacrylamide gel electrophoresis to transfer them onto a nitrocellulose membrane and blotted the membrane with anti-JNK antibody (Santa Cruz) or anti-IRAK antibody (Transduction Laboratories) to visualize using an enhanced chemiluminescent system (Dupont) (bottom figures of FIG. 10 and FIG. 11; WB). The result shows that CpG ODN activates JUN and IRAK of the macrophages derived from wild-type mice while it does not activate JUN and IRAK of the macrophages derived from TLR9 knockout mice (FIG. 10 and FIG. 11). It is therefore found that the signaling transduction mediated by CpG ODN depends on TLR9.

INDUSTRIAL APPLICABILITY

Bacteria-derived DNA comprising an unmethylated CpG motif significantly activates immune cells and induce Th1 response, while a receptor recognizing such bacterial DNA remained unknown. The present invention has revealed a receptor of oligonucleotides comprising an unmethylated CpG sequence of bacterial DNA and will enable us to elucidate a receptor protein TLR9, a member of TLR family, specifically recognizing bacterial DNA having an unmethylated CpG sequence, the genetic DNA encoding it or others, which will be useful to diagnose and treat bacterial diseases and others. The use of the TLR9 knockout animals will also enable us to elucidate functional mechanisms of DNA derived from bacteria at the molecular level.

What is claimed:

1. A transgenic mouse whose genome comprises a homozygous inactivation of the Toll-like Receptor 9 (TLR9) gene such that no functional N-terminal fragment of TLR9 is produced; said TLR9 gene encodes a polypeptide that recognizes CpG oligodeoxynucleotide (ODN), wherein macrophages of said mouse exhibit decreased responsiveness to CpG ODN.

2. A cell obtained from the transgenic mouse according to claim 1.

* * * * *

UNITED STATES PATENT AND TRADEMARK OFFICE
CERTIFICATE OF CORRECTION

PATENT NO. : 7,507,872 B2  
APPLICATION NO. : 10/088567  
DATED : March 24, 2009  
INVENTOR(S) : Akira et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (1067) days Delete the phrase "by 1067 days" and insert -- by 1008 days --

Signed and Sealed this

Twenty-second Day of December, 2009

David J. Kappos  
*Director of the United States Patent and Trademark Office*